US012577533B2

(12) United States Patent
Correa Rocha et al.

(10) Patent No.: US 12,577,533 B2
(45) Date of Patent: Mar. 17, 2026

(54) METHOD FOR OBTAINING REGULATORY T CELLS DERIVED FROM THYMIC TISSUE AND USE OF SAID CELLS AS CELL IMMUNOTHERAPY IN IMMUNE SYSTEM DISORDERS

(71) Applicant: FUNDACIÓN PARA LA INVESTIGACIÓN BIOMÉDICA DEL HOSPITAL GREGORIO MARAÑÓN, Madrid (ES)

(72) Inventors: Rafael Correa Rocha, Madrid (ES); Marjorie Pion, Madrid (ES); Esther Bernaldo De Quirós Plaza, Madrid (ES)

(73) Assignee: FUNDACIÓN PARA LA INVESTIGACIÓN BIOMÉDICA DEL HOSPITAL GREGORIO MARAÑÓN, Madrid (ES)

( * ) Notice: Subject to any disclaimer, the term of this patent is extended or adjusted under 35 U.S.C. 154(b) by 1428 days.

(21) Appl. No.: 16/977,044

(22) PCT Filed: Mar. 1, 2019

(86) PCT No.: PCT/EP2019/055221
§ 371 (c)(1),
(2) Date: Aug. 31, 2020

(87) PCT Pub. No.: WO2019/166658
PCT Pub. Date: Sep. 6, 2019

(65) Prior Publication Data
US 2021/0040450 A1    Feb. 11, 2021
US 2022/0306990 A2    Sep. 29, 2022

(30) Foreign Application Priority Data
Mar. 1, 2018    (ES) ............................... ES201830197

(51) Int. Cl.
| A61K 35/12 | (2015.01) |
| A61K 40/11 | (2025.01) |
| A61K 40/22 | (2025.01) |
| A61K 40/41 | (2025.01) |
| A61P 37/06 | (2006.01) |
| C12N 5/0783 | (2010.01) |

(52) U.S. Cl.
CPC ............ C12N 5/0637 (2013.01); A61K 40/11 (2025.01); A61K 40/22 (2025.01); A61K 40/416 (2025.01); A61K 40/418 (2025.01); A61P 37/06 (2018.01); C12N 5/0636 (2013.01); *A61K 2035/122* (2013.01); *C12N 2501/2302* (2013.01); *C12N 2501/51* (2013.01); *C12N 2501/515* (2013.01); *C12N 2509/10* (2013.01)

(58) Field of Classification Search
None
See application file for complete search history.

(56) References Cited

FOREIGN PATENT DOCUMENTS

| CN | 104619831 A | 5/2015 |
| EP | 2 711 418 A1 | 3/2014 |
| WO | WO 2012096376 A1 | 7/2012 |
| WO | WO 2018/165208 A1 * | 9/2018 |

OTHER PUBLICATIONS

Theedge (2024, pp. 1/6-6/6) (Year: 2024).*
Hardtke-Wolenski and Ladwehr-Kenzel (Mol. Cell. Ped, 2024, 11: 1-18) (Year: 2024).*
Opstelten and Amsen (Immunol. Let. 2021, 239: 96-112) (Year: 2021).*
Djike et al (Transplantation, 2012, 94(10): 357) (Year: 2012).*
Mauer et al (Cytotherapy, 2014, 16(4): S36) (Year: 2014).*
Safinia et al (Oncotarget, 2016, 7(7): 7563-7577) (Year: 2016).*
Macdonald et al (Transplantation, May 2017, 101 (5S-3), p. S9) (Year: 2017).*
Gregorczyk et al., "Significant expression of Foxp3 in murine extrathymic CD4+CD8+ double positive T cells," *Polish Journal of Veterinary Sciences* 20(4):815-817, Dec. 2017. (4 pages).
Huang et al., "Novel CD4+CD8+ Umbilical Cord Blood Regulatory T Cells," *Blood* 134(Supplement 1):4446, Nov. 2019. (3 pages).
Lee et al., "FoxP3+ T Cells Undergo Conventional First Switch to Lymphoid Tissue Homing Receptors in Thymus but Accelerated Second Switch to Nonlymphoid Tissue Homing Receptors in Secondary Lymphoid Tissues," *Journal of Immunology* 178:301-311, Jan. 2007. (11 pages).
Nunes-Cabaço et al., "Differentiation of human thymic regulatory T cells at the double positive stage," *European Journal of Immunology* 41:3604-3614, Sep. 2011. (11 pages).
Zou et al., "CD8+ Treg cells suppress CD8+ T cell-responses by IL-10-dependent mechanism during H5N1 influenza virus infection," *European Journal of Immunology* 44:103-114, 2014 [Published online Sep. 2013]. (12 pages).
Cosmi et al., "Human CD8+CD25+ thymocytes share phenotypic and functional features with CD4+CD25+ regulatory thymocytes," *Blood* 102(12):4107-4114, Dec. 2003. (8 pages).

(Continued)

*Primary Examiner* — Michael Szperka
*Assistant Examiner* — Marianne Dibrino
(74) *Attorney, Agent, or Firm* — Seed Intellectual Property Law Group LLP

(57) ABSTRACT

The present invention provides an in vitro method for obtaining and purifying regulatory T cells from thymic tissue (or thyTreg cells), which makes it possible to obtain more than 10 billion cells from a single thymus. These thyTregs obtained in the invention have a purity of more than 95% and very high suppressive capacity, survival and viability, in addition to being safe from a clinical viewpoint. The foregoing would not require the use of massive ex vivo cell expansion protocols. The transfer of these thyTreg cells to patients enables immune tolerance induction. Thus, said cells may be used as cell therapy to induce immune tolerance in the treatment and/or prevention of transplant rejections and in autoimmune diseases.

31 Claims, 8 Drawing Sheets

(56)                    References Cited

OTHER PUBLICATIONS

Bernaldo de Quirós et al., "Thymus-Derived Treg Infusion to Prevent Graft Rejection in Heart-Transplanted Children: Initial Exploration of a New Therapeutic Arsenal to Boost Immune Tolerance," *Transplantation* 101(5S-3):S36, 2017.

Bernaldo de Quirós et al., ""First-In-Human" Clinical Trial Employing Adoptive Transfer of Autologous Thymus-Derived Treg Cells (thyTreg) to Prevent Graft Rejection in Heart-Transplanted Children," *Transplantation* 102:S205, 2018.

Bluestone et al., "The therapeutic potential of regulatory T cells for the treatment of autoimmune disease," *Expert Opin. Ther. Targets* [*Early Online*]:1-13, 2015.

Brunstein et al., "Umbilical cord blood-derived T regulatory cells to prevent GVHD: kinetics, toxicity profile, and clinical effect," *Blood* 127(8):1044-1051, 2016.

Di Ianni et al., "Tregs prevent GVHD and promote immune reconstitution in HLA-haploidentical transplantation," *Blood* 117(14):3921-3928, 2011.

Dijke et al., "Discarded Human Thymus Is a Novel Source of Stable and Long-Lived Therapeutic Regulatory T Cells," *American Journal of Transplantation* 16(1):58-71, 2016.

Fraser et al., "A Rapamycin-Based GMB-Compatible Process for the Isolation and Expansion of Regulatory T Cells for Clinical Trials," *Molecular Therapy: Methods & Clinical Development* 8:198-209, 2018.

Hoffmann et al., "Loss of FOXP3 expression in natural human CD4$^+$CD25$^+$ regulatory T cells upon repetitive in vitro stimulation," *Eur. J. Immunol.* 39:1088-1097, 2009.

Lee et al., "T cells expressing CD19 chimeric antigen receptors for acute lymphoblastic leukaemia in children and young adults: a phase 1 dose-escalation trial," *Lancet* 385(9967):517-528, 2015.

Ma et al., "Adoptive transfer of double negative T regulatory cells induces B-cell death in vivo and alters rejection pattern of rat-to-mouse heart transplantation," *Xenotransplantation* 15:56-63, 2008.

MacDonald et al., "115.11 Development of GMP-Compatible Protocols for Thymus-Derived Regulatory T Cell Expansion," *Canadian National Transplant Research Program*, Wolters Kluwer Abstracts: S9, 2017.

Marek-Trzonowska et al., "Administration of CD4$^+$CD25$^{high}$CD127$^-$ Regulatory T Cells Preserves β-Cell Function in Type 1 Diabetes in Children," *Diabetes Care* 35:1817-1820, 2012.

Maude et al., "Chimeric Antigen Receptor T Cells for Sustained Remissions in Leukemia," *N. Engl. J. Med.* 371(16):1507-1517, 2014.

Miyara et al., "Functional Delineation and Differentiation Dynamics of Human CD4$^+$ T Cells Expressing the FoxP3 Transcription Factor," *Immunity* 30:899-911, 2009.

Safinia et al., "Regulatory T cells: serious contenders in the promise for immunological tolerance in transplantation," *Front Immunol.* 6(438):1-16, 2015.

Sakaguchi et al., "Regulatory T Cells and Immune Tolerance," *Cell* 133:775-787, 2008.

Sicard et al., "Cell therapy to induce allograft tolerance: time to switch to plan B?" *Frontiers in Immunology* 6(149):1-9, 2015.

Wiesinger et al., "Good Manufacturing Practice-Compliant Production and Lot-Release of Ex Vivo Expanded Regulatory T Cells As Basis for Treatment of Patients with Autoimmune and Inflammatory Disorders," *Frontiers in Immunology* 8(1371):1-17, 2017.

* cited by examiner

A) Frequency of thyTreg pre-purification

B) Frequency of viable cells in final product

C) Frecuency of thyTreg in final product

Activated T cells (without thyTreg)

Activated T cells (co-cultivated with thyTreg)

A)

B)

A)    Total thymocytes        B)    ThyTreg Final Product

C)    ThyTreg Final Product

A)

B)

A)  Protocol with Dynabeads

B)  Protocol with TransAct

C)

D)

A)

Standard conditions                Inflammatory conditions

B)

Standard conditions                Inflammatory conditions

METHOD FOR OBTAINING REGULATORY T CELLS DERIVED FROM THYMIC TISSUE AND USE OF SAID CELLS AS CELL IMMUNOTHERAPY IN IMMUNE SYSTEM DISORDERS

FIELD OF THE INVENTION

The present invention falls within the field of clinical immunology and cell immunotherapy, specifically within the protocols for obtaining and purifying regulatory T cells (Treg) that may be subsequently transferred to patients in cell therapy methods for the purpose of inducing immune tolerance, for example, in transplanted individuals or suffering from an autoimmune process.

BACKGROUND OF THE INVENTION

The main function that has long been attributed to the immune system is that of defending the organism from pathogenic agents. However, now we know that the immune system is also in charge of eliminating tumour cells and preventing the development of cancer, and it can also give rise to inadequate responses arising from the appearance of autoimmune processes, allergies or transplant rejections. The proper functioning of the immune system is only possible if there is a balance or homeostasis adequate thereto, such that an excessive response will give rise to pathologies such as allergies or rejection and a deficient response would enable the progression of infections and cancer.

In recent years we have witnessed the appearance of revolutionary cell therapies with immune cells in cancer treatment, which seek to induce or restore specific immune responses to a tumour and compensate the patient's immune deficiency that is responsible for these pathologies. Such is the case of "CAR T cell" technology, in which the patient's immune cells are genetically modified to attack the tumour in a specific manner. Companies like Novartis or Gilead have developed this cell therapy to treat B leukemias, achieving a remission of approximately 80%, and this therapy has been recently approved by the FDA and also by the EMA, which represents an authentic revolution in cancer treatment (Maude S. L., et al., 2014, N Engl J Med., 371 (16): 1507-17; Lee D. W., et al., 2015, Lancet, 385 (9967): 517-528).

However, no cell therapies with similar effectiveness in the opposite sense, i.e. inducing immune tolerance to prevent or cure autoimmune diseases or allogeneic graft rejection, have been developed. Immunotherapies have not yet been developed that reduce excessive immune responses and restore immune tolerance with clear success. Autoimmune diseases and immune rejection are currently treated with immunosuppressive drugs. Since the appearance of these drugs in the 1960s, the practice of transplants became viable but, despite improvements in these drugs, they still do not offer a definitive solution to rejection and continue to cause side effects that are determining factors in the clinical evolution of the patient. Specifically, long-term immunosuppression causes chronic toxicity which, in addition to significantly influencing the patient's quality of life, affects the fulfilment of the treatment, the overall success rate and the survival of the patient and the graft. Since most immunosuppressors act in a non-selective way, the entire system is repressed and/or deregulated, losing its capacity to defend the host against infections or the propagation of tumour cells, or producing vascular damage that causes the failure of the transplanted organ. Additionally, during childhood, the constant administration of immunosuppressors can interfere in normal development and in the proper maturity of the immune system that occurs during that period, which may have lifelong consequences upon altering the patient's immune capacity. These immunosuppressive drugs are likely to continue to improve in the future, further reducing rejection rates; however, the downside of this strategy will always be the deterioration and chronic damage caused to the immune system. Even with better prevention of graft rejection, the disorders related to the deterioration of the immune system, such as infections, cancer and autoimmune diseases will continue to limit the long-term survival of transplant patients receiving immunosuppressive drugs.

To this end, achieving immune tolerance that will indefinitely avoid rejection or autoimmune diseases that affect millions of people has become the major challenge of modern medicine.

The current opinion of the science community is that just one immune tolerance induction that involves re-educating the immune responses of the transplant recipient will allow the indefinite survival of the graft or prevent and cure autoimmune processes. This tolerance induction would make it possible to tolerate the transplanted organ without need for pharmacological immunosuppression, thereby eliminating the toxic effects of these therapies and their damaging effects on the immune system.

One of the most promising alternatives for increasing the life expectancy of transplant patients is to induce immune tolerance by means of cell immunotherapy, which would allow the indefinite survival of the graft without the morbidity associated with immunosuppressive treatments (Sicard A., et al., 2015, Front Immunol; 6:149). This approach focuses on deliberately reducing the specific immune response to the graft, while eliminating or significantly reducing long-term pharmacological suppression, thereby maintaining a competent immune system. Immune tolerance is an essential characteristic of the immune system and the discovery of a subset of lymphocytes with suppressive capacity capable of inducing this tolerance is generating widespread enthusiasm in the clinical sphere. These cells, called regulatory T cells (Treg), constitute an essential part of the immune system and could play a crucial role in the prevention of graft rejection or autoimmune diseases and the maintenance of immune homeostasis beneficial to patients. Tregs are capable of suppressing the effector function of a wide range of cells, including T CD4+ and CD8+, NK cells, B cells, macrophages and dendritic cells (Sakaguchi S., et al., 2008, Cell; 133:775-87). Consequently, Treg cells have become an interesting field of study of autoimmunity, allergy and also transplants.

Cell therapy with Tregs is therefore postulated to become the great hope in the treatment of diseases mediated by an excessive or inadequate response of the immune system, such as autoimmune processes (Bluestone J. A., et al., 2015, Expert Opin. Ther. Targets; 19:1091-103), graft-versus-host disease in bone marrow transplant patients (Brunstein C. G., et al., 2016, Blood; 127:1044-51) or transplant rejection (Safinia N., et al., 2015, Front Immunol; 6:438).

The basic role of Tregs in transplants has been confirmed by various studies in animal models of skin and heart transplants, demonstrating that the Tregs present in the receptacle at the time of the transplant are critical to the induction and maintenance of tolerance to the graft (Wood K. J., Sakaguchi S., 2003, Nat. Rev. Immunol.; 3:199-210). These Treg cells will impede the activation and expansion of effector T cells, which are responsible for cellular rejection.

Additionally, Tregs can also induce the death of B cells, preventing humoral rejection, as already demonstrated in a cardiac xenotransplantation model (Ma Y., et al., 2008, Xenotransplantation; 15:56-63).

Current knowledge in the field points to the hypothesis that immune tolerance in transplant patients or with auto-immune processes is determined by the balance of Treg cells over effector T cells. Therefore, it is expected that a greater number of circulating Tregs will be capable of preventing the activation and proliferation of effector cells that trigger these diseases.

Therefore, a therapeutic strategy that could offer excellent results in the prevention of rejection or in the treatment of autoimmune processes would be to carry out cell therapy through Treg cell transfer, in order to substantially increase their number in the circulation and thus potentiate the recipient's intrinsic mechanisms of tolerance in the recep-tacle to the transplanted organ or to own tissues. The transfer of autologous Tregs in patients is achieved by drawing blood from the patient, purifying the Tregs present in said blood, expanding these Tregs ex vivo to obtain an appropriate number and transferring the expanding autologous Tregs back to the patient. As discussed below, other groups have demonstrated their effectiveness in the prevention of rejec-tion in animal models and clinical trials have even been performed in other diseases that confirm their therapeutic use in humans.

The safety and potential effectiveness of Treg therapy in humans is reflected in the first Phase-I/II trials already performed. Most clinical trials with Tregs have been per-formed within the context of bone marrow transplants in patients with haematological neoplasies, showing that the infusion of Tregs in these patients reduces or prevents graft-versus-host disease (GvHD) (Brunstein C G. et al., 2016, Blood. 127 (8): 1044-51; Di Ianni M. et al., 2011, Blood. 117 (14): 3921-8). The greatest risk of GvHD occurs in the first three months and immune suppression through Treg therapy during this short period has proven to be sufficient to provide long-term tolerance. However, in the case of solid organ transplants or autoimmune diseases, the risk persists throughout the life of the patient or graft, which requires the protective effect of the Tregs to persist in time in order to ensure the prevention of inadequate immune responses.

There is an international consortium, called The One Study, which is carrying out a multicentric Phase I/II study in which the safety and potential effectiveness of the infu-sion of ex vivo expanded Tregs in the context of liver and kidney transplants in adults. However, although the prelimi-nary results of this consortium are promising, they evidence the difficulties of obtaining quality Tregs from peripheral blood and the limited survival and effectiveness of Tregs present in adult patients because of their more differentiated phenotype (Safinia N., et al., 2015, Front Immunol., 6:438). There are also Treg transfer trials in other diseases such as type-I diabetes, including a trial in children (Marek-Tr-zonowska N., et al., 2012, Diabetes Care; 35:1817-20). But despite the great interest and expectation generated in recent years by this therapeutic alternative, treatment with Treg cells still fails to offer definitive results in the prevention of solid organ rejection in humans.

Most of the strategies and trials carried out to date use Treg cells obtained from peripheral blood, which are sub-sequently expanded ex vivo and transferred back to the patient as cell therapy. The greatest limitation is to achieve a sufficient number of Tregs, since their frequency in periph-eral blood is very low (4-10% of total T CD4+ lymphocytes), due to which it is essential to apply massive ex vivo Treg expansion protocols before being able to transfer the cells back to the patients. Wiesinger et al., 2017, Frontiers in Immunology, 8:1371 describe a GMP-compliant production of ex vivo expanded Treg cells isolated from peripheral blood. This method comprises CD8+ cell depletion prior to CD3/CD28 stimulation.

Another important limitation is that the Treg cells present in the peripheral blood of adults are differentiated cells and may have a high degree of senescence. These more differ-entiated cells have a survival limited to a few months, reduced suppressive capacity, phenotypical instability that can make them lose the expression of the Foxp3 molecule that determines the functionality and suppressive capacity thereof, and can even be differentiated to pro-inflammatory effector T cells (Miyara M., et al., 2009, Immunity; 1-13). If these cells are also expanded in culture their regulatory cell capacity is further reduced (Hoffmann P., et al., 2009, Eur. J. Immunol.; 39:1088-97).

Ex vivo Treg cell expansion protocols therefore have various problems that limit their usefulness for obtaining functional cells that can be successfully and safely used in human clinical trials:

a. Most expansion protocols do not fulfil the mandatory GMP (Good Manufacturing Practice) requirements for the cells obtained to be used in immunotherapy in humans.

b. It has been demonstrated that, depending on the initial Treg phenotype, ex vivo expansion can lead to the loss of the suppressive capacity thereof. Treg cells with in vitro-stimulated memory phenotype lose the Foxp3 expression (responsible for their suppressive capacity) and their Treg phenotype, while Tregs with naïve phenotype are capable of maintaining the Foxp3 expression and, therefore, their suppressive capacity after repeated stimulation and expansion. This fact has been confirmed by various authors, indicating that the population of naïve Treg cells, whose proportion is a minority in adults, would be the most appropriate for being expanded, preserving the suppressive properties thereof.

c. The in vitro expansion of differentiated Treg cells or with memory phenotype can lead to the loss of the suppressive phenotype thereof and acquire a proinflam-matory-secreting cytokine phenotype such as IL-17 or IL-4, which could even worsen or favour the organ rejection process.

That is, the difficulties encountered to obtain the adequate quantity and quality of Tregs using current strategies limit the clinical usefulness of this therapy. Therefore, ongoing human trials for inducing tolerance through Treg transfer are encountering great difficulty in generating enough cells and with the necessary suppressive capacity to obtain a clear therapeutic effect in the short and long term.

To date, the use of Treg therapy to prevent solid organ rejection in humans has not produced definitive clinical results. The limited number of Tregs in peripheral blood that may be purified, together with the low survival and limited suppressive capacity of the Tregs obtained from adults, have probably compromised the success of this therapeutic strat-egy.

A recently published "proof of concept" demonstrates that human thymic tissue, as an alternative to peripheral blood, is a potential source of Treg cells that enables the obtainment of cells with an optimal phenotype (Dijke I. E., et al., 2016, American Journal of Transplantation, 16:58-71; and Mac-Donald K. et al. 2017, Wolters Kluwer, Canadian national transplant research program, page S9). This study, which proposes the use of thymic tissue as a source of Tregs, confirms the quality of the cells obtained from this tissue, the suppressive capacity thereof and the larger number of available cells with respect to the use of peripheral blood as a source of the cells. However, since it is an in vitro research study in which animal models are used, it applies the Treg purification protocols commonly used in research, which includes the use of bovine serums, enzyme treatments, depletion of CD8 using complement-mediated lysis, rapamycin, particles coated with non-human anti-CD3 and anti-CD28 antibodies as Treg activators, etc., some of which are incompatible with the subsequent use of the cells obtained as immunotherapy in humans. Additionally, the number of Treg cells obtained using this method is still insufficient to implement an adequate treatment in humans.

Based on the foregoing, there is a need to develop optimised methods for obtaining and purifying Treg cells that will make it possible to obtain cells with improved quality in terms of phenotype, purity, preserved suppressive capacity, survival and viability, in addition to an adequate and sufficient number of cells for the subsequent use thereof in immunotherapy in humans. Also, said methods must provide cells that are safe from a clinical viewpoint for use thereof in cell immunotherapy in humans. The therapeutic use of the Treg cells obtained by means of said enhanced methods would make it possible to prevent chronic immune rejection, thereby achieving prolonged transplant survival.

SUMMARY OF THE INVENTION

As above-mentioned, one of the greatest limitations to Treg-based cell therapy is to achieve a sufficient number of Tregs. To date, the protocols for purifying Tregs from peripheral blood obtain yields of less than 20 million cells, thereby requiring massive expansion protocols that involve the use of different reagents and that significantly reduce the quality of the cells.

The inventors provide for the first time a protocol for the obtaining of Treg cells wherein CD8+ cells are not depleted prior to CD3/CD28 stimulation. This has been shown by the inventors to result in the presence of a CD4+CD8+ population of Foxp3+ Tregs in the final product (aprox. 41%, FIG. 4B, 4C). Considering that around 80% of the thymocytes present in the thymic tissue are cells expressing CD4 and CD8 markers (FIG. 4A), a previous CD8-depletion as employed in other protocols will discard most of these CD4+CD8+ Treg cells.

In preferred embodiments, a colloidal polymer nanomatrix conjugated with humanised CD3 and CD28 agonists is used for CD3/CD28 activation, this is an innovative approach which provides levels of Treg cells activation and expansion comparable to those obtained using CD3/CD28 beads (FIG. 6) while enabling the T cell activator to be easily removed from the culture media thus minimizing the loss of Treg cells in this step.

As shown in the Examples, the protocol of the invention for the obtaining of Treg cells from isolated thymus tissue enabled to obtain more than 13 billion thyTregs with a purity of more than 95% (see FIGS. 1C and 4B), a viability of more than 80% (FIG. 1B) and a very high suppressive capacity (FIGS. 2 and 3). Such a number of cells would make it possible to prepare more than 1,000 doses of cell therapy for a patient less than 1 year old and hundreds of doses if used in older children or in adults. These yields in obtaining thyTreg cells are unheard of.

Accordingly, in a first aspect, the invention relates to an in vitro method for obtaining a regulatory T (Treg) cell population from isolated thymic tissue comprising the following steps:

a. mechanically disaggregating the thymic tissue;
b. filtering the product obtained after stage (a), and resuspending the precipitate comprising thymocytes in a culture medium;
c. isolating CD25+ cells from the product obtained after stage (b);
d. culturing the cell population obtained after stage (c) in a culture medium in the presence of a T cell activator and IL-2 or TGFβ (preferably IL-2), preferably wherein said T cell activator comprises at least CD3 and CD28 agonists; and
e. removing the T cell activator from the culture medium of stage (d);
f. optionally, further culturing the regulatory T cells in a culture medium in the presence of IL-2 or TGFβ (preferably IL-2);

with the proviso that prior to step (d) the cell population has not been depleted from CD8+ cells.

Another aspect of the invention relates to a regulatory T cell or population of regulatory T cells obtained or obtainable through the method of the invention.

A further aspect of the invention relates to the thyTreg cells and thyTreg cell population of the invention as described herein, for use as a medicament.

An additional aspect of the invention relates to a pharmaceutical composition comprising the thyTreg cells and thyTreg cell population of the invention as described herein, wherein said pharmaceutical composition further comprises an excipient and/or pharmaceutically acceptable carrier.

Another aspect of the invention relates to a kit (hereinafter, "first kit of the invention") comprising all the necessary reagents, mediums and means to carry out the method of the invention as described herein.

Still a further aspect of the invention relates to a kit (hereinafter, "second kit of the invention") comprising the thyTreg cell or thyTreg cell population of the invention as described herein, or the pharmaceutical composition of the invention as described herein and an adequate medical device for the administration, preferably for injection, of cells to an individual.

DESCRIPTION OF THE INVENTION

In a first aspect, the invention provides an in vitro method for obtaining and purifying a new subtype of Treg cells obtained from thymic tissue. In another aspect, the invention refers to a Treg cell or Treg cell population obtained in accordance with the method herein described and which are called "thyTregs" in the present invention.

Figure 6:
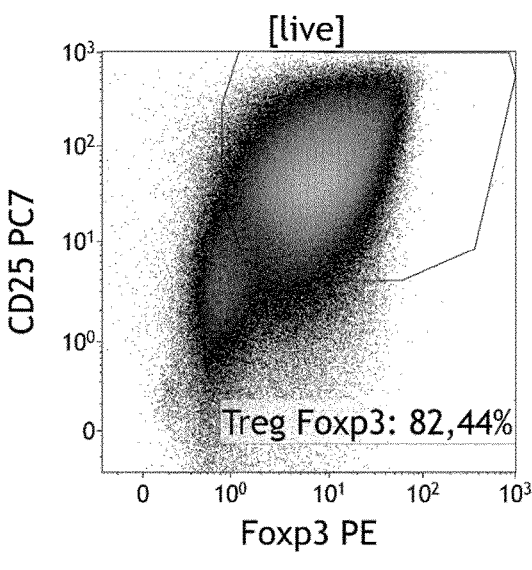
FIG. 6. Differences in purity of CD25+Foxp3+ cells (A-B), in the expression of functional Treg markers (C), and in the fold expansion (D) between the same protocol employing Dynabeads CD3/CD28 CTS™ or T Cell Trans-Act™ as a cell activator.
Figure 6:
Figure 6:
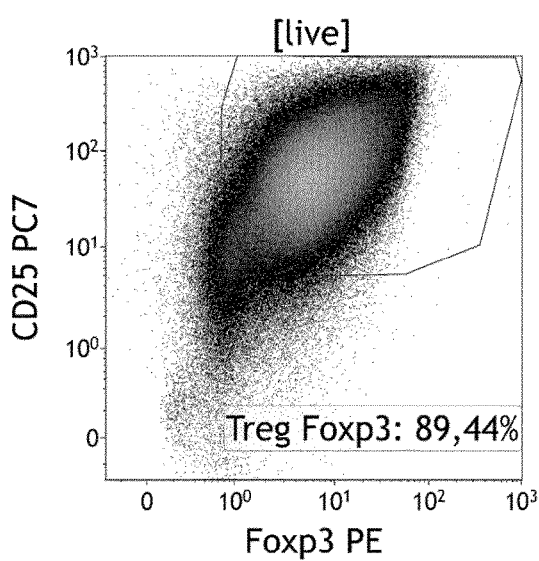
Figure 6:
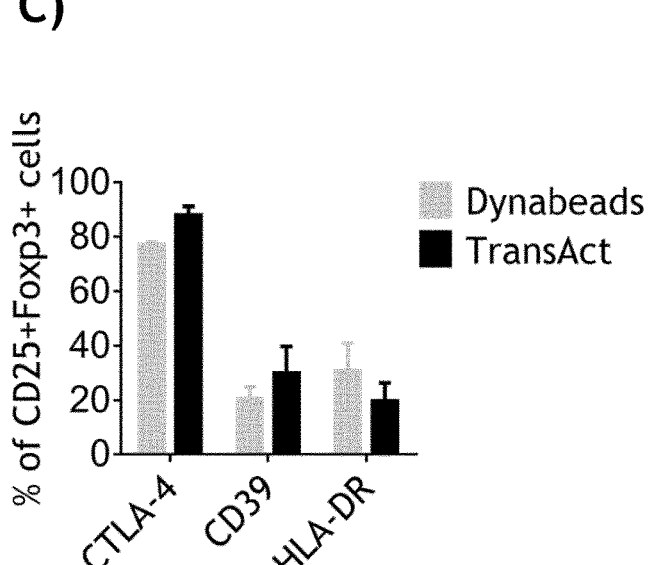
Figure 6:
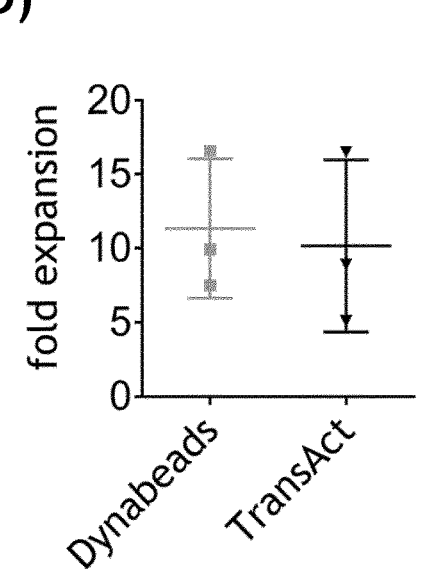

The thyTregs obtained by the method of the invention, as opposed to the Tregs present in blood or obtained by other methods, have been shown to present differential characteristics that make them optimal for their clinical use in cell therapy. Thus, they have greater capacity to suppress effector cells of the immune system, an undifferentiated phenotype (since cells contained in the thymus have not yet been exposed to foreign antigens), high viability and a stable expression of Foxp3 (FIG. 8A), stable IL-10 production (FIG. 8B), and adequate expression of functional markers such as CTLA-4 and CD39 (FIG. 6C). Additionally, the protocol for obtaining, purifying and processing thyTreg developed herein makes it possible to produce more than 10.000 millions ($1×10^{10}$) thyTregs (see, for instance, Example 1 where more than 13.000 millions thyTregs are obtained) from a single thymus, with a purity of more than 95%. These figures are very superior to those that can be obtained from a single individual using other methods, whether from peripheral blood (Safinia N., et al., 2015, Front Immunol., 6:438) or thymic tissue as a source of the cells (Dijke I. E., et al., 2016, American Journal of Transplantation, 16:58-71).

The dose of Tregs commonly used in therapeutic trials in adults is approximately $1-10×10^6$ Tregs/kg of the patient's weight. The yield of the protocol herein described would therefore make it possible to generate more than 1,800 doses of thyTreg cells from a single thymus for, for example, a 6 month-old paediatric patient (6-8 kg). This not only makes it possible to perform the treatment without need for massive cell expansion, but there would still be a sufficient number of cells to store several frozen doses that could be used in future re-infusions in the patient, in the event of appearance of any sign of rejection, or for use in other patients (allogeneic use).

As explained earlier, massive numbers of thyTreg cells have been obtained with the protocol of the invention and said method is also compatible with the GMP conditions required for the subsequent use of the obtained cells as therapy in humans. Additionally, the thyTregs obtained in the invention may have a purity of more than 95% and very high suppressive capacity, survival and viability. Said Treg cells population and yields have been obtained without using products or methods that make them incompatible with the subsequent clinical use thereof in humans. This therapeutic approach therefore makes it possible to modulate immune homeostasis in the long term and not only in the early stages of the pathological process. The transfer of thyTreg cells obtained with the method of the invention to patients therefore may achieve indefinite immune tolerance induction, i.e. throughout the life of the graft.

Using thymic tissue as a source of the cells, preferably removed from paediatric heart transplant patients, a specific protocol has been developed through which massive numbers of thyTreg cells are obtained, with an optimal phenotype, high suppressive capacity and longer average life, without need for massive ex vivo expansion protocols that would alter their qualities. The cells thus obtained can be used for autologous or allogeneic transfer to patients, such as transplant patients, preferably solid transplant patients, more preferably paediatric heart transplant patients. In this manner, the intrinsic mechanisms of immune tolerance are activated. The results obtained indicate that this cell immunotherapy could definitively prevent immune rejection of the graft, with the ensuing reduction or complete elimination of the administration of immunosuppressive drugs and the toxicity associated therewith. Also, said therapeutic strategy opens a new frontier in the treatment of other types of disorders related to the immune system, such as autoimmune processes.

The present invention therefore makes it possible to overcome the barriers existing to date that have limited the success of therapy with Treg cells in humans, preferably within the context of solid organ transplants, and provides a solution to the need to provide optimised methods for obtaining and purifying Treg cells that make it possible to obtain cells that are safe from a clinical viewpoint in an adequate and sufficient number for the subsequent use thereof in cell immunotherapy in humans, preferably with an enhanced suppressor phenotype sustained in time, enhanced purity, preserved suppressor capacity, high survival and viability.

Some of the most outstanding advantages of the method of the present invention and of the thyTreg cells obtained therethrough are, therefore, as follows:

In preferred embodiments, the described method does not perform any type of enzyme digestion, or use reagents, animal serums or products incompatible with the subsequent therapeutic use of the cells obtained, as opposed to other similar protocols described in the state of the art in which the culture medium is supplemented with bovine or human serums that render the subsequent clinical use of the cells impossible. The use of particles coated with anti-CD3 and anti-CD28 antibodies in the Treg culture medium to activate the cells is also common in the state of the art (see, for example, Dijke I. E., et al., 2016, American Journal of Transplantation, 16:58-71). However, the presence of this type of reagents requires complex additional methods to completely eliminate the aforementioned particles before transferring the cells to the patient. On the contrary, preferred embodiments of the method of the invention only use reagents allowed in the production of cells for therapeutic use, due to which it is 100% compatible and safe, thereby allowing the clinical and therapeutic use of the cells.

The method makes it possible to obtain larger amounts of Treg cells (more than 10 billion thyTreg cells from a single thymus) in comparison to the methods of the state of the art, especially those in which peripheral blood is used as a source of the cells or that described in Dijke I. E., et al., 2016, American Journal of Transplantation, 16:58-71, wherein only around 300 million cells are obtained (insufficient from a clinical viewpoint). This offers the possibility of preparing various doses that can be administered to the patient at different time intervals or can be preserved for future autologous or allogeneic administration.

The method does not require massive ex vivo cell expansion, such that the quality of the cells and the phenotype responsible for suppressive capacity (sustained Foxp3 expression) are maintained.

The method enables differentiation of immature Treg cells (with low expression of Foxp3) into a stable and desirable Foxp3+ Tregs.

Thy Treg cells can be produced with a purity of 95% and without the presence of effector T cells that not only do not have suppressive capacity, but can even induce rejection or an inflammatory response. The Treg cells are usually isolated using CD25 antibodies, a molecule present in the Tregs, but they also express the T CD4+ effector cells. Therefore, in current methods the purified population contains contaminating effector cells that do not have suppressive capacity and have an inflammatory effect. The advantage of the method of the invention is that, since the cells contained in the thymus have not been exposed to foreign antigens, there are no effector cells and, therefore, all purified cells will be thyTreg cells, since they express CD25.

The thyTreg cells obtained have high survival (higher than average life) and a viability of more than 80%, even 90% (FIG. 1B).

The thyTreg cells obtained have excellent suppressive capacity, higher than 70%, since they have a sustained Foxp3 expression. This is relevant for the immune tolerance induced in the patient after the transfer of these cells to persist in time and provide indefinite protection against immune rejection (long-term immune tolerance of the transplant).

The thyTreg cells obtained have an optimal suppressive phenotype, enhanced with respect to Treg cells obtained from peripheral blood (Dijke I. E., et al., 2016, American Journal of Transplantation, 16:58-71).

Figure 8:
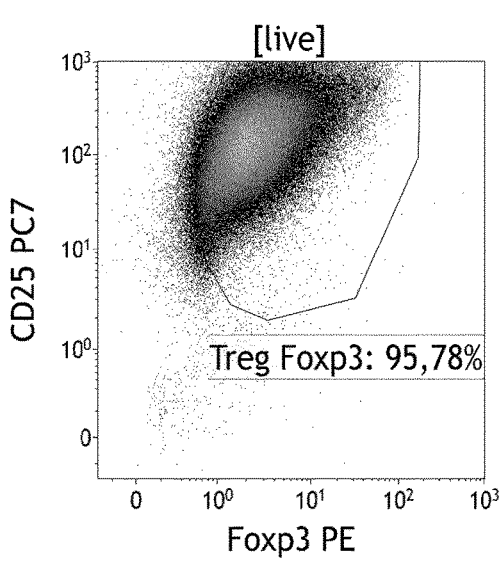
FIG. 8. ThyTreg produced with our protocol maintain stable expression of Foxp3 (A) and IL-10 production capacity (B) in the presence of pro-inflamatory cytokines (IL-1β, IL-6, TNFα; Inflammatory conditions) in comparison with the standard culture conditions.
Figure 8:
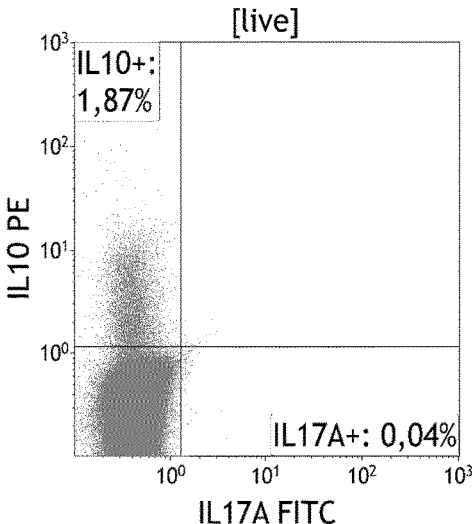
Figure 8:
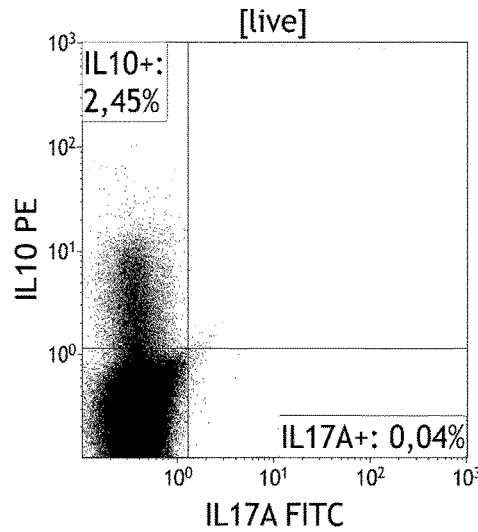

Additionally, this protocol of the invention uses thymic tissue, wherein the Treg cells are produced, as a source of the cells instead of peripheral blood. The main advantage of the thyTreg cells obtained from this tissue is that, on not having ever migrated to the periphery, they all have a naïve and undifferentiated phenotype, thereby having greater survival, and are capable of maintaining the Foxp3 expression and its suppressive capacity after repeated stimulation and expansion. The naïve Treg cells, whose proportion is minority in adults, are therefore the most appropriate for use in cell therapy, maintaining their suppressive capacity. In this respect, the analyses made by the inventors of the present invention demonstrate that the thyTregs obtained with the protocol herein described:

a. have a survival up to ten times higher than that of the adult Treg cells obtained from peripheral blood, b. have excellent suppressive capacity, suppressing the proliferation of TCD4 and TCD8 effector cells by more than 70%, even 75% (see examples of the invention shown below), c. maintain the Foxp3 expression after in vitro activation and a stable suppressive phenotype, and d d. maintain the Foxp3 expression and IL-10 production capacity even in the presence of cytokines (IL-1β, IL-6, TNFα) that normally are able to switch the Treg phenotype towards Th17 cells (FIG. 8).

Another advantage represented by the method of the invention is that the thymic tissue, which is usually removed and discarded during heart surgeries such as heart transplants or different operations to palliate congenital heart diseases, can be easily available for use as a source of Tregs, preferably autologous but also for the allogeneic use thereof.

Additionally, the administration of thyTreg cells obtained with the method of the invention makes it possible to reduce or completely eliminate the use of immunosuppressive drugs which, due to their nonspecific activity repressing the entire immune system, have associated high chronic toxicity and side effects such as the development of infections, tumour processes or autoimmune diseases.

Furthermore, the possibility of using the patient's own cells (autologous administration of thyTregs) significantly decreases the potential side effects arising from the therapeutic use of allogeneic cells. Additionally, this strategy is a low-cost therapy that could be placed at patients' disposal in a relatively short period of time.

In summary, the therapeutic strategy herein described makes it possible to prevent transplant rejection, have indefinite survival of the graft and have greater life expectancy for the transplant patients, particularly in children. Additionally, it open the possibility of implementing a biobank of thyTreg cells obtained with the method of the invention from thymic tissues, preferably discarded in heart surgeries, which would make it possible to develop a cell therapy with allogeneic thyTregs for the treatment of various immune-related diseases, such as autoimmune disorders or graft-versus-host disease, by inducting immune tolerance.

In a first aspect, the invention relates to an in vitro method for obtaining a regulatory T (Treg) cell population from isolated thymic tissue comprising the following steps:

a. mechanically disaggregating the thymic tissue;

b. filtering the product obtained after stage (a), and resuspending the precipitate comprising thymocytes in a culture medium;

c. isolating CD25+ cells from the product obtained after stage (b);

d. culturing the cell population obtained after stage (c) in a culture medium in the presence of a T cell activator and IL-2 or TGFβ (preferably IL-2), preferably wherein said T cell activator comprises at least CD3 and CD28 agonists; and e. removing the T cell activator from the culture medium of stage (d);

f. optionally, further culturing the regulatory T cells in a culture medium in the presence of IL-2 or TGFβ (preferably IL-2);

with the proviso that prior to step (d) the cell population has not been depleted from CD8+ cells.

Depletion of CD8+ cells can be conducted for instance using complement-mediated lysis. In preferred embodiments, the thymocytes population has not been depleted from CD8+ cells prior to the CD25+ cells isolation step.

The term regulatory T (Treg) cell as used herein refers to a cell characterized by expressing CD4, CD25 and Foxp3 cell surface markers, also referred as CD4+CD25+Foxp3+ cells. Preferably, a Treg cell population obtained by the method of the invention is characterized by comprising at least 80%, preferably at least 85%, more preferably at least 90%, 95%, 97%, or 99% of CD4+CD25+Foxp3+ cells.

Preferably, step a) comprises mechanically disaggregating the thymic tissue in the presence of a culture medium and without using enzymes, for instance by the use of a tissue dissociator as described herein below.

This method will also be referred to in the present description as the "method of the invention".

The isolated thymic tissue can be found, prior to carrying out the method of the invention, stored in a sterile receptacle comprising a saline solution, such as, but not limited to, sodium chloride and antibiotics and antifungals.

In a preferred embodiment, optionally in combination with one or more of the features or embodiments described herein, the method of the invention comprises a step prior to stage (a) that comprises dividing the isolated thymic tissue into smaller parts or sections, more preferably into parts of between 2-3 grammes.

The method of the invention is carried out, preferably, in a GMP-approved cell production unit, which ensures the biosafety of the cells finally obtained.

Preferably, the method of the invention does not comprise the use of reagents such as bovine serum or proteins derived therefrom, human serum, enzymes, anti-CD28 or anti-CD3 coated beads or rapamycin.

The "thymic tissue" to which the present invention relates is any tissue sample from the thymus, which is the gland of the lymphatic system where T cells or lymphocytes mature, located in front of the heart and behind the breastbone. The thymic tissue can be removed by any method known in the art that serves such purpose, such as for example by means of a thymectomy, which can be transsternal, transcervical or videoscopic. Preferably, the thymic tissue is removed, prior to carrying out the method of the present invention, during a surgical intervention, more preferably intended for treating a heart disease, such as for example congenital heart disease, or during a heart transplant. Even more preferably, the thymic tissue of the invention is removed during a paediatric heart transplant.

The thymic tissue can come from a human or a non-human mammal such as, for example, but not limited to, rodents, pigs, primates, ruminants, felines or canines. In a preferred embodiment of the method of the invention, the thymic tissue comes from a human, more preferably a human aged between 0 (newborn) and 16 years, even more preferably between 0 and 10 years, particularly between 0 and 24 months.

In another preferred embodiment, the thymic tissue comes from the same individual to whom the thyTreg cells obtained at the end of the method of the invention are going to be subsequently administered for cell immunotherapy. That is, the tissue is preferably autologous.

In the present invention, "paediatric patient" or "child" is understood to be a human aged between 0 and 16 years, preferably between 0 and 10 years, even more preferably between 0 and 24 months.

The "tissue dissociator" that can be used in the method of the invention is one that allows the mechanical disaggregation of the tissue without using enzymes. Any tissue dissociator from among those commercially available in the state of the art could be used in stage (a) of the method of the invention. Examples of these dissociators are, but not limited to, the gentleMACS™ Dissociator or the gentleMACS™ Octo Dissociator from Miltenyi Biotec, the TissueLyser LT from Quiagen or tissue dissociators from Worthington Biochemical, Sigma-Aldrich or Roche Diagnostics. Preferably, the tissue dissociator used in the present invention is the gentleMACS™ Octo Dissociator from Miltenyi Biotec.

In step (a) of the method of the invention, the thymic tissue previously removed may be mechanically disaggregated using a tissue dissociator, which is a unit that preferably allows semi-automated and standardised tissue dissociation, giving rise to cell suspensions. The samples of the tissue to be dissociated can be added to receptacles, preferably disposable, that make it possible to prepare and handle the sample in a closed and sterile system, providing a high level of safety and minimising the risk of contamination. Said receptacles may also contain GMP culture medium, and preferably antibiotic, for instance at a concentration from 2% to 20%, preferably from 2% to 10%, more preferably 5% of antibiotic. Examples of antibiotics that may be present and used in the present invention are, but not limited to, penicillin, streptomycin, amphotericin or any combination thereof. The GMP culture medium is free of serums and components derived from animals, allows cultivation and expansion of human and mouse T cells and the expansion of the thyTreg cells of the invention.

A "GMP (Good Manufacturing Practice) culture medium" is any cellular culture medium that has been approved for the maintenance of cells in culture medium, preferably T cells, more preferably human T cells, that will subsequently be used in human clinical studies, preferably in cell therapy. A GMP culture medium does not comprise animal-derived components, it is serum-free and fulfils GMP requirements. Examples of this type of culture mediums are, but not limited to, X-Vivo™ 15 (Lonza, Ref. BE02-060), ImmunoCult™-XF T Cell Expansion Medium (StemCell Technologies, Ref. 10981) or TexMACS™ GMP Medium (Miltenyi Biotic, Ref. 170-076-307). Preferably, the GMP culture medium used in the method of the invention further comprises antibiotic. The antibiotics that are usually present in the culture medium are, for example, those cited in the preceding paragraph. More preferably, the GMP culture medium used throughout this method is TexMACS™ medium from the company Miltenyi Biotic, even more preferably comprising antibiotic. Examples of suitable antibiotics and antibiotic concentrations are as provided herein above.

The "TexMACS™ culture medium" comprises salts, amino acids, fatty acids, vitamins, pharmaceutical grade human albumin (i.e. GMP or suitable for use in humans) and buffer. The pH of this medium is maintained, preferably, within a range between 6.9 and 7.3 and may or may not comprise phenol red.

Once stage (a) has been completed, the product obtained from the tissue disaggregation is filtered, preferably using filters with a pore diameter of 30-40 μm, more preferably wherein said filters are made of nylon mesh to remove tissue remnants and aggregates and obtain uniform single-cell suspensions. Subsequently, the resulting product can be (optionally) centrifuged. Finally, the cellular precipitate comprising thymocytes is resuspended in the GMP culture medium preferably containing antibiotic, for instance at a concentration from 2% to 20%, preferably from 2% to 10%, more preferably 5% of antibiotic. With this suspension of thymocytes obtained, a cell quality and viability control can optionally be performed using the methods known in the art and, typically if viability is greater than 80% and there are no signs of contamination, it proceeds to the next stage of the method of the invention, which consists of purifying the Treg cells. Otherwise, the sample would be discarded.

In stage (c) of the method of the invention, CD25+ cells (which comprise the Treg cells) are isolated or purified from the product obtained in the previous stage. The purification of this stage (c) can be carried out using, for example, but not limited to, any immunocytochemical techniques known in the art that enable the positive selection or isolation of cells expressing specific markers in its surface. The CD25+ cell population may for instance be isolated by flow cytometry or using magnetic cell separators. Although not yet approved by the regulatory agencies, single-use and close circuit cell sorters are being developed which may be suitable for the production of cells for human therapy purposes). In preferred embodiments, optionally in combination with one or more of the features or embodiments described herein, step (c) comprises the use of magnetic beads conjugated to antibodies against CD25.

This purification step is preferably carried out in a clean room environment and by means of a cell purification system authorised for use in cell therapy in humans, preferably using the CliniMACs® instrument, more preferably in the presence of buffer solutions, such as 0.9% of sodium chloride supplemented with antibiotics or TexMACS™ medium or others, and a specific murine IgG1 isotype anti-human CD25 monoclonal antibody conjugated with superparamagnetic particles, more preferably CliniMACs® CD25 reagent. That is, the product obtained in the previous stage is introduced in the purification system, preferably in the CliniMACs® system. The "CliniMACs®" or "CliniMACs® plus" instrument is commercially available from the company Miltenyi Biotic and is an automated cell separation platform and a functionally closed, sterile system. The "CliniMACS® CD25 reagent" consists of a specific mouse IgG1 isotype anti-human CD25 monoclonal antibody conjugated with superparamagnetic iron dextran particles and is preferably contained in a non-pyrogenic sterile solution. Said reagent is commercially available from the company Miltenyi Biotic and makes it possible to enrich CD25+ cells from heterogeneous human cell populations when used in combination with the CliniMACS® instrument or system. Once CD25+ cells (comprising the Treg cells) are purified in the method of the invention, a quality control can optionally be performed using, for example, but not limited to, flow cytometry to verify the viability, number and purity of the Treg cells obtained.

A "system for purifying cells authorised for use in cell therapy in humans" is any instrument capable of isolating and purifying specific cell populations from a heterogeneous cell suspension containing different cell types. These instruments must be based on the isolation and purification of the cells of interest according to the molecules or specific cellular markers expressed on the surface thereof and it is essential for these instruments to preserve the viability and functional capacity of the cells once purified. Additionally, these instruments must be GMP-authorised for therapeutic use in humans. Examples of these cell purifying systems authorised for use in cell therapy in humans are, but not limited to, CliniMACs® plus (Miltenyi Biotec), CliniMACs@ Prodigy (Miltenyi Biotec), RoboSep™ (STEMCELL Technologies), MACSQuant® Tyto® (Miltenyi Biotec) or MoFlo® Astrios™ Sorter (Beckman Coulter), preferably CliniMACs® plus (Miltenyi Biotec).

At the end of step (c) cell viability and purity of CD25+ cells in the obtained cell population is typically analysed. Preferably, cell viability is of at least 80%, preferably at least 85%, 90%, 95%, 97% or at least 99%. Also, purity of CD25+ cells is preferably of at least 70%, preferably at least 75%, 80%, 85%, 90%, 95%, 97% or at least 99%. In a preferred embodiment, cell viability is of at least 80% and purity of CD25+ cells is of at least 70%.

In stage (d) of the method of the invention, the Treg cells purified in the previous stage are cultivated in the presence of a T cell activator. Step (d) can be conducted during 1 to 5 days, preferably for at least 2 or 3 days, more preferably for at least three days.

A "T cell activator" is any product which allows the in vitro stimulation and proliferation of T cells, preferably human, through its interaction with T cell activation receptors, for example by joining CD3/CD28. Activation of T cells can be determined for instance by determining expression of CD25 and/or CD69, such as by using flow cytometry. Preferably, activation of Treg cells can be assessed by determining the expression of CD25 and/or Foxp3. Preferably, said T cell activator comprises at least CD3 and CD28 agonists. The term "agonist" is used herein to refer to a ligand that binds to a receptor and activates the receptor. Examples of T cell activators are, but not limited to, MACS GMP T Cell TransAct™ human (Miltenyi Biotec, Ref. 170-076-156), which comprises a colloidal polymeric nanomatrix as defined herein, particles coated with anti-CD3 called Dynabeads CD3/CD28 CTS™ (ThermoFisher, Ref. 40203D) and antibody complexes such as the anti-CD3/CD28 and anti-CD3/CD28/CD2 antibody tetramers used by MacDonald et al. 2017 (Wolters Kluwer, Canadian national transplant research program, page S9).

The term "antibody" as used herein may refer to an immunoglobulin or an antigen-binding fragment thereof. Unless otherwise specified, the term includes, but is not limited to, polyclonal, monoclonal, monospecific, multispecific, humanized, human, chimeric, synthetic, recombinant, hybrid, mutated, grafted, and in vitro generated antibodies. In certain embodiments, the term "antibody" may also refer to antibody derivatives, such as antibody-based fusion proteins or antibodies further modified to contain additional non-proteinaceous moieties, such as water soluble polymers, e.g. polyethylene glycol (PEG).

Preferably, the T cell activator used in the present invention is the T Cell TransAct™ human reagent, which comprises a colloidal polymer nanomatrix. Said T cell activator is a colloidal polymeric nanomatrix conjugated with humanized CD3 and CD28 agonists, more preferably the T Cell TransAct™ human reagent. For the culture, the Treg cells can be added to any culture receptacle useful for cultivating human cells. The "T Cell TransAct™ human" reagent is commercially available from the company Miltenyi Biotec and is useful for activating and expanding human T cells. Said reagent comprises a nanomatrix which is a colloidal polymeric nanomatrix conjugated with agonists humanized for CD3 and CD28, supplemented with a phosphate buffered saline (PBS) and containing poloxamer 188 and recombinant human serum albumin. Its pH is maintained, preferably, within a range between 7.3 and 7.9. This nanomatrix facilitates the efficient activation of T cells while maintaining the viability thereof. The use of a polymeric nanomatrix for CD3/CD28 activation allows sterile filtering and removal of the excess reagent by simply replacing the supernatant or by a washing step, e.g., by centrifugation. This T Cell Trans- Act™ human reagent has been designed to activate T cells, however, in the present invention the doses have been adapted for producing the activation of the Treg cells. Thus, preferably, the doses of the T cell activator (e.g., the T Cell TransAct™ human) used in this stage of the method of the invention range between 1.10 and 1:100. Also present at this cultivation step are a culture medium (preferably a GMP culture medium, more preferably TexMACS™ medium), wherein said medium preferably comprises antibiotic (e.g., 5% of antibiotic), and further comprises interleukin 2 (IL-2) or TGFβ, preferably IL-2.

Cells can be cultured in step (d) in the presence or absence of rapamycin. For instance rapamycin concentrations of 50 ng/ml to 200 ng/ml, preferably about 100 ng/ml, can be used. In preferred embodiments, the cells are cultured in step (d) in the absence of rapamycin.

In step (e) of the method of the invention, the T cell activator is removed, preferably by centrifuging the culture of the previous stage. The T cell activator can be removed, according to step (e) of the method of the invention, by means of, for example, but not limited to, centrifugation, column separation, etc., preferably by means of centrifugation. Said centrifugation is carried out, more preferably, at 1,500 rpm for 10 minutes at room temperature.

Subsequent to this removal, the cells can optionally be maintained under culture for at least another one to seven days, preferably for at least, another four days, regularly renewing the culture medium with antibiotic and IL-2. Expanding the cells during one additional day may provide the highest purity rates but the number of Treg cells will be lower than after having expanded these for two, three, or preferably four days.

Cells can be cultured in step (f) in the presence or absence of rapamycin. For instance rapamycin concentrations of 50 ng/ml to 200 ng/ml, preferably about 100 ng/ml, can be used. Preferably, the cells are cultured in step (f) in the absence of rapamycin.

In steps (d) and (f) IL-2 may be used at a concentration from 50 to 2000 IU/ml, preferably from 100 to 1000 IU/ml, more preferably from 500 to 700 IU/ml, such as about 500 IU/ml or 600 IU/ml.

Preferably, in the culturing steps of the method of the invention said culture medium is a GMP culture medium.

After the cultivation of stages (d) and/or (f) of the method of the invention, a cell quality, sterility and safety control can be performed. Also, the cultivated cells can be distributed in different doses for storage and/or transport.

As explained earlier, the large number of thyTreg cells that can be obtained with the protocol of the invention makes it possible to store doses for future allogeneic or autologous administrations. Thus, in the other preferred embodiment, the method of the invention further comprises an additional step (g) comprising the storage, more preferably cryopreservation, of all or part of the thyTreg cells obtained after the cultivation of step (f) or after step (e). Even more preferably, this storage takes place in sterile receptacles, preferably vials, of equal or different doses therebetween. "Cryopreservation" can be carried out preferably between −80° C. and −196° C.

In a particular embodiment the invention relates to an in vitro procedure, protocol or method for obtaining regulatory T cells from isolated thymic tissue (or thyTreg cells) comprising the following stages:

a. mechanically disaggregating the thymic tissue using a tissue dissociator, preferably a gentleMACS™ Octo Dissociator, in the presence of GMP culture medium, preferably TexMACS™ medium, b. filtering (and preferably subsequently centrifuging) the product obtained after stage (a) and resuspending the precipitate comprising thymocytes in the GMP culture medium, preferably TexMACS™ medium, c. purifying the Treg cells from the product obtained after stage (b) by means of a cell purification system authorised for use in cell therapy in humans, preferably using a CliniMACs® plus instrument, more preferably in the presence of a specific murine IgG1 isotype anti-human CD25 monoclonal antibody conjugated with superparamagnetic particles, even more preferably in the presence of CliniMACs® CD25 reagent, d. cultivating, for at least three days, the Treg cells obtained after stage (c) in the presence of a T cell activator, of GMP culture medium, preferably TexMACS™ medium, and IL-2, wherein the T cell activator is more preferably a colloidal polymeric nanomatrix conjugated with humanised CD3 and CD28 agonists, even more preferably the T cell activator is T Cell TransAct™ human reagent, e. removing the T cell activator from the culture medium of stage (d), preferably the nanomatrix used in stage (d) by, more preferably, centrifuging said culture medium, and f. optionally, keeping the thyTreg cells obtained in culture medium for at least another four days.

Another aspect of the invention relates to a regulatory T cell or population of regulatory T cells (hereinafter, "regulatory T cell of the invention", "thyTreg cell of the invention" or "thyTreg cell population of the invention"), obtained or obtainable through the method of the invention. In a particular embodiment, said thyTreg cell of the invention expresses at least the markers CD4, CD25 and Foxp3. That is, the thyTreg cells of the invention are CD4+, CD25+ and Foxp3+. In another embodiment, a thyTreg cell population obtained by the method of the invention is characterized by comprising at least 80%, preferably at least 85%, more preferably at least 90%, 95%, 97%, or 99% of CD4+ CD25+Foxp3+ cells.

The Treg cells or the Treg cell population of the invention may also express the markers CTLA-4 and CD39. In some embodiments, at least 30%, 40%, 50%, 60%, 70% or at least 80% of the cells in the cell population of the invention express CD39 and/or CTLA-4.

"Expression" in the present invention is understood to be protein or mRNA expression, preferably protein.

The thyTreg cell of the invention expresses the aforementioned cell markers typical of the aforementioned Treg cells (CD4+, CD25+ and Foxp3+); however, it also has functional and structural features that differentiate it from other Treg cells isolated, expanded, purified and/or activated using methods other than the method of the invention. It is well known in the art that cell gene expression profiles and, as a consequence of the cellular functions thereof, differ depending on the protocol used to cultivate them and stimulate or activate them in vitro. Thus, the method of the invention uses specific culture conditions and reagents that affect the gene expression profile and the properties of the thyTreg cells finally obtained.

As explained previously in the present description, these cells of the invention may have: i) greater suppressive capacity (they suppress more than 70% or even 75% of the proliferation of activated T CD4+ and T CD8+ cells); ii) an expression of Foxp3 stable over time; iii) higher survival; iv) greater frequency of IL-10 production cells; v) an undifferentiated and optimal phenotype; vi) expression of Foxp3 stable and preserved IL-10 production in the presence of pro-inflamatory cytokines such as IL-1β, IL-6, or TNFα, which are able of switching the phenotype of other Treg cells obtained using other methods. Therefore, said cells of the invention are clearly different from other Treg cells obtained by other methods of the state of the art.

In preferred embodiments, the cell population obtained by the method of the invention has a viability of at least 80%, preferably at least 85%, more preferably at least 90%, 95%, 97%, or 99%. Cell viability may be determined by any method known in the art, for instance by excluding dead cells on the basis of scatter signals and/or using fixable or non-fixable viability dyes for flow cytometry.

Also in preferred embodiments, the cell population of the invention has a suppressive capacity of at least 60%, preferably at least 65%, 70%, 75%, or preferably 80% or more of the proliferation of activated T CD4+ and T CD8+ cells. Suppresive capacity can be determined by any methods known in the art and for instance by comparing T cell activation in the presence or absence of the Treg cell population as shown in Example 2.

The thyTreg cells of the invention may also be genetically modified by any of the methods known in the art. For instance, ThyTreg cells may be modified using gene editing technologies (such as CRISP/CAS9) to eliminate immunogenic molecules and obtain "universal" ThyTreg cells. Such universal ThyTreg cells would be particularly useful for allogeneic use. The present invention also provides the possibility of developing generations of CAR thyTreg cells, i.e. thyTreg cells genetically modified to express a chimeric antigen receptor, such that they would be antigen-specific. Thus, personalised therapies could be created with the thyTreg cells of the invention that specifically and exclusively suppress the effector cells that react to the antigens of the transplanted organ or to the autoantigens that mediate autoimmune processes in each patient.

Thus, in a preferred embodiment, the thyTreg cell or population of thyTreg cells of the invention comprise a recombinant nucleic acid sequence encoding, and expressing, a chimeric antigen receptor. Hereinafter, this cell will be referred to as "CAR thyTreg of the invention". Said nucleic acid sequence can be introduced in the cell in a recombinant manner by means of known molecular biology techniques.

The "chimeric antigen receptor" or "CAR" is a T cell membrane receptor artificially introduced, and expressed, in the thyTreg cell of the invention by means of genetic engineering. Said chimeric receptor is joined to a desired antigen present in another target cell, preferably in an effector T cell to be suppressed. These receptors are called chimeric due to being composed of parts of different molecules. The expression of chimeric antigen receptors is achieved by transferring the nucleic acid sequence encoding the receptor of interest to the thyTreg cell of the invention through the use of, for example, but not limited to, viral vectors.

The "antigen or epitope" recognised by the chimeric receptor can be, but is not limited to, a protein or protein fragment, a carbohydrate or a glycolipid. More preferably, this antigen or epitope is a molecule present in (i.e. expressed by) an effector cell of the immune system, even more preferably expressed on the surface by an effector cell of the immune system, wherein even more preferably said effector cell of the immune system is specific, i.e. it attacks epitopes present in an organ transplanted to the host organism or autoantigens present in the organs or tissues of the host organism itself. Thus, preferably, the CAR thyTreg cell of the invention thus generated acquires the capacity to recognise and suppress the effector cells of the immune system that are attacking epitopes present in the transplanted organ or autoantigens.

"Effector cell of the immune system" is understood to be, for example, but not limited to, a T CD4 or CD8 lymphocyte, NK cells, B cells, macrophages, phagocytes, neutrophils, basophiles and eosinophils, or dendritic cells. Preferably, the effector cell of the immune system to which the present invention relates is a T CD4 or T CD8 lymphocyte.

The thyTreg cells of the invention (including genetically modified cells derived therefrom), the cell population of the invention or the CAR thyTreg cell of the invention can be directly administered to an individual for use as a medicament, such as for immune tolerance induction or can be added to pharmaceutical compositions for use as a cell therapy medicament.

Therefore, another aspect of the invention relates to a pharmaceutical composition (hereinafter, "composition of the invention" or "pharmaceutical composition of the invention") comprising the thyTreg cell, the CAR thyTreg cell or the population of thyTreg cells of the invention, preferably in a therapeutically effective number.

The expression "therapeutically effective number" makes reference to the number of cells of the invention that produces the desired effect. The dose for obtaining a therapeutically effective number depends on a variety of factors such as, for example, age, weight, sex, pathological condition or tolerance of the individual to whom the composition of the invention is going to be administered. Preferably, the therapeutically effective amount of cells of the invention comprised in the composition of the invention is between 1 and 20 million cells (1-20×10$^6$) per kg of weight of the individual.

In another preferred embodiment, this pharmaceutical composition of the invention further comprises an excipient and/or pharmaceutically acceptable carrier. Said pharmaceutical composition can further comprise another active ingredient and/or an adjuvant.

The term "excipient" refers to a substance that aids the absorption of the elements of the composition of the invention, stabilises said elements, an activates or aids the preparation of the composition in the sense of, for example, giving it consistency. Therefore, the excipient could have the function of maintaining the viability of the cells comprised in the composition and/or the suppressive properties thereof, etc., or the protective function of the composition such as, for example, to isolate it from air and/or humidity, without excluding other types of excipients not mentioned in this paragraph.

The "pharmaceutically acceptable carrier", like the excipient, is a substance used in the composition to dilute any of the components of the present invention comprised therein up to a certain volume or weight. The pharmacologically acceptable carrier is an inert substance or with a similar action to any of the elements of the present invention. The function of the carrier is to facilitate the incorporation of other elements, enable better dosage and administration or give the composition consistency and form. When the presentation form is liquid, the pharmacologically acceptable carrier is the dilute. Pharmacologically acceptable carriers that could be used in the present invention may be liquid, such as water, solvents, oils or surfactants, including those of petroleum, animal, plant or synthetic origin.

The term "adjuvant" refers to an agent without antigenic effect itself but that can stimulate the effect of the composition of the invention. There are many known adjuvants in the state of the art such as, for example, but not limited to, aluminium phosphate, aluminium hydroxide, toll-like receptor agonists, cytokines, squalene, incomplete Freund's Adjuvant or complete Freund's Adjuvant.

As used herein, the term "active principle", "active substance", "pharmaceutically active substance", "active ingredient" or "pharmaceutically active ingredient" means any component that provides a pharmacological activity in the cure, mitigation, treatment or prevention of a disease or pathological condition, or that affects the structure, metabolism, or function of the bodies of humans or other animals. The active ingredient to which the present invention relates may be, for example, but not limited to, one or more immunosuppressive drugs or one or more anti-inflammatory agents. The active ingredient may be a therapeutic agent commonly used to treat autoimmune diseases, transplant rejection or graft-versus-host disease, i.e. an "immunosuppressive drug" such as, but not limited to, calcineurin inhibitors (cyclosporine, tacrolimus), mTOR inhibitors (sirolimus, everolimus), anti-proliferative agents (azathioprine, methotrexate, mycophenolic acid), monoclonal antibodies (Daclizumab, Basiliximab), corticosteroids, anti-thymocyte and anti-lymphocyte globulin, or any combination thereof, provided that these active ingredients are not incompatible with the survival and functionality of the cells of the invention comprised in the pharmaceutic composition.

The pharmaceutical composition of the invention can also be presented in the form of sustained release formulation together with a carrier. The term "sustained release" refers to a vehiculisation system that provides the gradual release of the cells comprised in the composition during a period of time and preferably, although not necessarily, with relatively constant release levels throughout said period of time. Illustrative examples of sustained release systems include, although not limited to liposomes, mixed liposomes, oleosomes, niosomes, ethosomes, millicapsules, microcapsules, nanocapsules, sponges, cyclodextrines, vesicles, micelles, mixed surfactant micelles, mixed phospholipid-surfactant micelles, millispheres, microspheres, nanospheres, lipospheres, microemulsions, nanoemulsions, miniparticles, milliparticles, microparticles, nanoparticles, lipidic solid particles and nanostructured lipidic mediums.

The pharmaceutic composition of the invention can be administered to an animal, including a mammal and preferably to a human, in a variety of forms including, but not limited to, parenteral, intraperitoneal, intravenous, intradermal, epidural, intraspinal, intrastromal, intraarticular, intrasynovial, intrathecal, intralesional, intraarterial, intracardiac, intramuscular, intranasal, intracranial, subcutaneous, intraorbital, intracapsular, by means of transdermal patches, percutaneous, nasal spray, surgical implant, internal surgical paint, infusion pump, via catheter or by direct injection in the patient's lymph nodes. Preferably, the pharmaceutical composition of the invention is formulated for the intravenous administration thereof.

The pharmaceutical composition of the present invention may be adapted for application by means of medical devices that enable the release of the cells comprised therein in adequate concentrations for immune tolerance induction. These devices can be adequate for the local administration of the composition, such that it acts in the affected area, preventing the treatment from dispersing. These devices can, for example, but not limited to, carry the pharmaceutical composition of the invention in its interior or be coated with it. These devices include, for example, circulatory assistance, endovascular procedure and cardiovascular surgery devices and, among these, for example, but not limited to, stents, valves, rings, sutures, patches or vascular grafts.

Another aspect of the invention relates to a kit (hereinafter, "first kit of the invention") comprising all the necessary reagents, mediums and means to carry out the method of the invention as described earlier. Preferably, said kit comprises: (i) a GMP culture medium, preferably TexMACS™ medium, more preferably also comprising antibiotic as described earlier; (ii) response of one or more specific antibodies to the expression of surface markers by the thyTreg cells of the invention such as, for example, to CD4, CD25, Foxp3, CTLA-4 and/or CD39 molecules, preferably the kit comprises anti-CD25 antibodies, more preferably a specific murine IgG1 isotype anti-human CD25 monoclonal antibody conjugated with superparamagnetic particles, even more preferably the kit comprises the CliniMACs® CD25 reagent; (iii) a T cell activator, preferably a colloidal polymeric nanomatrix with humanised CD3 and CD28 agonists, more preferably T Cell TransAct™ human reagent; and optionally (iv) IL-2. In another preferred embodiment, said kit also comprises filters, preferably with a pore diameter comprised between 30 and 40 μm, more preferably wherein said filters are made of nylon mesh. In another preferred embodiment, said kit further comprises saline o buffer solution, preferably sodium chloride, antibiotics, antifungals or any other agent to prevent the contamination of cultivated cells or tissues, one or more sterile receptacles to contain the thymic tissue and/or the cell suspensions, one or more vials for the storage and/or cryopreservation of the thyTreg cells obtained and/or one or more receptacles for the in vitro cultivation of Treg cells. Said kit may also comprise the instructions for carrying out the method of the invention.

Another aspect of the invention relates to the use of this first kit of the invention to carry out the method of the invention.

Another aspect of the invention relates to a kit (hereinafter, "second kit of the invention") comprising the thyTreg cell, the CAR thyTreg cell or the population of thyTreg cells of the invention or the pharmaceutical composition of the invention and an adequate medical device for the administration, preferably for injection, of cells in an individual.

An "adequate medical device for injecting cells in an individual" is any device or instrument that can be useful for injecting cells into the bloodstream or in a tissue. Examples of this type of devices or instruments are, but not limited to, syringes, vials, catheters, needles, cannulas or, in general, any instrument that can be used in cell therapy, including those known in the state of the art.

The cells of the invention or the pharmaceutical composition of the invention can be encapsulated, for example in vials with the same or different doses, in the second kit of the invention. Also, said elements can be marked and/or immobilised in a medium of any type in said kit.

Additionally, the second kit of the invention may comprise other elements, such as culture mediums and/or reagents, useful for in vitro or ex vivo maintenance of the cells of the invention or of the composition of the invention. Said kit may further comprise elements that help to prevent the contamination of the cells comprised therein, such as antibiotics, bacteriostatics, bacteroides, antifungal agents, etc.

In general, the second kit of the invention comprises all the necessary reagents to, in accordance with the present invention, perform immune tolerance induction in an individual. Furthermore, this second kit can include all the necessary mediums and receptacles for the start-up and optimisation thereof. Preferably, this kit further comprises instructions for injecting the cells or the pharmaceutical composition of the invention in an individual.

Another aspect of the invention relates to the use of the thyTreg cell, of the CAR thyTreg cell or of the population of thyTreg cells of the invention or of the pharmaceutical composition of the invention to elaborate a drug. Alternatively, this aspect of the invention relates to the thyTreg cell, the CAR thyTreg cell or the population of thyTreg cells of the invention or to the pharmaceutical composition of the invention for use as a medicament.

The term "medicament" refers to any substance used to prevent, alleviate, treat or cure diseases or pathological conditions in humans and animals. The medicament to which the present invention relates can be for human or veterinary use. The "medicament for human use" is any substance or combination of substances that is presented as having properties for treating or preventing diseases or pathological conditions in humans or that can be used in humans or be administered to humans for the purpose of restoring, correcting or modifying the physiological functions, preferably of the immune system, exercising a pharmacological, immune or metabolic action. The "medicament for veterinary use" is any substance or combination of substances presented as having curative or preventive properties with respect to the animal diseases or pathological conditions or that can be administered to the animal for the purpose of restoring, correcting or modifying its physiological functions, preferably of the immune system, exercising a pharmacological, immune or metabolic action.

The term "treatment" refers to combating the effects caused as a consequence of the disease or pathological condition of interest in a patient (preferably a mammal and more preferably a human) which includes:

(i) inhibiting the disease or pathological condition, i.e. halting its development;

(ii) alleviating the disease or pathological condition, i.e. causing the regression of the disease or the pathological condition or its symptoms;

(iii) stabilising the disease or the pathological condition.

The term "prevention" consists of preventing the appearance of the disease or pathological condition, i.e. preventing the disease or the pathological condition from occurring in a patient (preferably a mammal and more preferably a human), particularly when said patient has predisposition to the pathological condition but it has not yet been diagnosed as such.

The medicament of the invention could be administered, but without serving as a limitation, by means of a transplant at systemic level or by means of a local injection in the affected tissue.

In a preferred embodiment of this aspect of the invention, the medicament is a cell therapy medicament, more preferably a cell immunotherapy medicament.

"Cell therapy" or "cytotherapy" is understood to be the therapy in which cellular material or cells are administered to an individual, in the context of the present invention, living thyTreg cells of the invention.

Preferably, the medicament to which the present invention relates is for the adoptive transfer of thyTreg cells, CAR thyTreg cells or the population of thyTreg cells of the invention to an individual, wherein said cells can be of autologous or allogeneic origin to said individual, although more preferably are autologous.

"Autologous" cells are understood to be those which have been obtained from the same individual to whom they are going to subsequently be administered after their treatment or modification with the method of the invention. Thus, the term "autologous" implies the same individual as a donator and receptor.

Preferably, in the present invention, the thymic tissue that is used as starting material in the method of the invention has been removed from the same individual that will subsequently benefit from the cell immunotherapy, administering the drug or pharmaceutical composition of the invention.

Contrarily, "allogeneic" is understood to be those cells, tissues, organs or biological samples in general which have been obtained from an individual other than the receptor individual.

In another preferred embodiment, the medicament of the invention is intended for inducing or restoring the immune tolerance of an individual, more preferably in an individual who has undergone a transplant or graft, or who has an autoimmune condition, or an inflammatory process, or an allergy or graft-versus-host disease. In general, the medicament of the invention is intended for treating and/or preventing any situation in which the activity of the immune system must be decreased or suppressed in an individual.

In another preferred embodiment, the medicament of the invention is intended for treating and/or preventing a pathological condition associated with an excessive response, undesired or inadequate response of the immune system. More preferably, wherein the pathological condition is selected from the list consisting of: autoimmune disease, inflammatory processes, allergy, graft-versus-host disease and/or immune rejection in transplanted individuals. Alternatively, this aspect of the invention relates to the thyTreg cell, the CAR thyTreg cell, the population of thyTreg cells, the pharmaceutical composition of the invention for use thereof in the treatment and/or prevention of a pathological condition selected from the list consisting of: autoimmune disease, inflammatory processes, allergy, graft-versus-host disease and/or immune rejection in transplanted individuals. In a particular embodiment, the pathological condition is an autoimmune disease.

Examples of "autoimmune diseases" that could be treated and/or prevented with the medicament of the invention are, but not limited to, type I diabetes, arthritis (such as, for example, rheumatoid arthritis, psoriatic arthritis, ankylosing spondylitis or juvenile idiopathic arthritis), multiple sclerosis, intestinal inflammatory affection of autoimmune origin (such as Chron's Disease or ulcerative colitis), vasculitis (such as Wegener's Disease or atherosclerosis), asthma, inflammatory autoimmune affection of the bile duct (such as primary biliary cirrhosis or primary sclerosing cholangitis), autoimmune thyroiditis (Hashimoto's Disease), hyperthyroidism (Graves's Disease), autoimmune adrenal insufficiency (Addison's Disease), autoimmune oophoritis, autoimmune orchitis, autoimmune hepatitis, autoimmune haemolytic anaemia, paroxysmal cold haemoglobinuria, autoimmune thrombocytopenia, autoimmune neutropenia, pernicious anaemia, pure red cell aplasia, autoimmune coagulopathies, myasthenia gravis, autoimmune polyneuritis, pemphigus and other blistering disorders, rheumatic heart disease, Goodpasture Syndrome, postcardiotomy syndrome, lupus erythematosus, Sjögren Syndrome, polymyositis, dermatomyositis, sclerodermia, chronic obstructive pulmonary diseases, chronic inflammatory diseases, celiac disease, Churg-Strauss Syndrome, cardiovascular disease, polydermatomyositis, septic shock, rhinitis, psoriasis, cancer-associated cachexia, eczema, Vitiligo, Reiter Syndrome, Kawasaki's Disease, idiopathic thrombocytopenia purpura, Guillain-Barré Syndrome, antiphospholipid antibody syndrome (APS) or narcolepsy.

In the context of the present invention, the term "allergies" includes, but is not limited to, food allergies to, for example, milk and egg proteins, pollen, mites, mould and fungus spores, animal fur, insect bites or medicaments.

Furthermore, the "transplanted or grafted individuals" to whom the present invention relates include both clinically transplant patients and animal models used in experimentation subjected to an allo- or xenograft or allo- or xenotransplant of an organ or tissue.

The "transplant" or "graft" to which the present invention relates is, preferably, allogeneic or xenogeneic and relates both to transplanted cells and complete organs, parts of organs or tissues.

"Graft-versus-host disease" (GvHD) is the pathological immune condition that may arise after a bone marrow or hematopoietic stem cell transplant.

In another preferred embodiment of this aspect of the invention, the individual with the pathological condition, more preferably the individual subjected to a transplant or who has an autoimmune disease or condition is human. Even more preferably, the human is a child or paediatric patient aged between 0 and 16 years, preferably between 0 and 10 years, more preferably between 0 and 24 months. In the case that the autologous thyTreg cells of the invention are used for the treatment, the human is preferably a paediatric patient. In the case that the allogeneic thyTreg cells are used for the treatment, the human is preferably a patient of any age, including adults.

In another preferred embodiment, the medicament of the invention is intended for treating and/or preventing immune rejection in transplanted individuals. More preferably, the transplant is a solid organ transplant.

"Solid organ transplant" is understood to be the transplant of an organ and not of tissue, such as bone marrow or isolated cells. Examples of solid organs are, but not limited to, the heart, kidneys, liver, prostate, spleen, lungs, glands such as the pancreas, skin, cornea, bone, digestive tract, etc. More preferably, the solid organ to which the present invention relates is the heart.

In a particular embodiment, the medicament of the invention is used for treating and/or preventing the immune rejection in paediatric cardiac (preferably heart) transplant patients, wherein said medicament comprises thyTreg cells of the invention or CAR thyTreg cells of the invention of autologous origin.

The medicament of the invention can be used both alone and in combination with other drugs or compositions for immune tolerance induction, or for treating and/or preventing a pathological condition selected from the list consisting of: autoimmune disease, inflammatory processes, allergy, graft-versus-host disease and/or immune rejection in transplanted individuals. These other medicaments or compositions to be administered as therapy combined with the medicament of the invention can form part of the same composition or can be administered by means of different compositions, and can be administered simultaneously with the medicament of the invention or at different times.

Therefore, in another preferred embodiment, the medicament of the invention is administered in combination with at least one immunosuppressive drug and/or with at least one anti-inflammatory drug, more preferably with at least one immunosuppressive drug. Said administration may be simultaneous or sequential. Preferably, the administration is sequential, more preferably the immunosuppressive drug is firstly administered in one or more doses distributed over time and next, preferably seven days after having initiated the treatment with immunosuppressive drugs, the medicament of the invention is administered while gradually reducing or fully eliminating the administration of immunosuppressive drugs. Therefore, in a more preferred embodiment, the medicament of the invention is administered once a previous therapy with immunosuppressive drugs has been completed. At the moment of administering the medicament of the invention, the administration of immunosuppressive drugs can be completely eliminated to give way to the exclusive treatment with the medicament of the invention, or the dose of said immunosuppressive drugs can be gradually decreased until completely eliminated. The immunosuppressive drugs are, preferably, those described earlier in the present description.

Another aspect of the invention relates to a method for inducing or restoring immune tolerance in an individual, more preferably in a transplanted or grafted individual, or who has an autoimmune condition, or in an inflammatory process or an allergy or graft-versus-host disease, wherein said method comprises the administration of the thyTreg cell of the invention, the CAR thyTreg cell of the invention, the population of thyTreg cells of the invention or the pharmaceutical composition of the invention to said individual, more preferably in a therapeutically effective number.

Another aspect of the invention relates to a method for treating and/or preventing a pathological condition selected from the list consisting of: autoimmune disease, inflammatory process, allergy, graft-versus-host disease and/or immune rejection to a transplant, wherein said method comprises the administration of the thyTreg cell of the invention, the CAR thyTreg cell of the invention, the population of thyTreg cells of the invention or the pharmaceutical composition of the invention to an individual suffering from said pathological condition.

Throughout the description and the claims, the word "comprises" and its variants do not intend to exclude other technical features, additives, components or steps. For the persons skilled in the art, other objects, advantages and features of the invention shall be partly inferred from the description and partly from the practice of the invention. The following examples and figures are provided by way of example and are not intended to limit the scope of the present invention.

EXAMPLES

The invention is illustrated below by trials performed by the inventors, which evidence the effectiveness of the method of the invention in obtaining and purifying thyTreg cells useful for the subsequent therapeutic use thereof in cell immunotherapy by inducing immune tolerance.

Example 1. Protocol for Obtaining and Purifying
thyTreg Cells from Human Thymic Tissue The protocol herein described was developed in the IISGM Immune-Regulation Laboratory for purifying Treg cells from thymic tissue (thyTreg cells) removed from paediatric patients during heart surgeries. The protocol makes it possible to obtain a massive number of thyTreg cells with very high purity and optimal phenotype. The protocol is also GMP-compatible and fulfils the requirements for the subsequent use of the cells as immunotherapy in humans.

The phases of the protocol are as follows:
1. Removal and transport of the thymic tissue.
2. Disaggregation of the tissue and obtainment of thymocytes.
3. Purification of the Treg cells.
4. Cultivation and activation of the thyTreg cells.

1.1. Removal and Transport of the Thymic Tissue

The thymic tissue is usually removed to access the heart during paediatric heart transplants and other congenital heart disease surgeries. Given the large size of the thymus in young children, which completely covers the heart, surgeons are obliged to remove it to free up the surgical field and therefore this tissue, which is normally discarded, can be used as a source of thyTregs in paediatric heart transplant patients or for an allogeneic use of immunotherapy with thyTreg cells in other patients and pathologies.

The thymus removed in the operating theatre was collected in sterile receptacles containing 50 ml of a saline solution of 0.9% sodium chloride and supplemented with antibiotics and antifungals (Sigma, Cat. No. A5955). The receptacle, hermetically sealed and protected inside a plastic biosafe receptacle, was transported to the GMP-certified Cell Production Unit for processing thereof.

1.2. Disaggregation of the Tissue and Obtainment of Thymocytes

Following the necessary biosafety protocols and fulfilling the specific requirements for GMP production of cells, the thymic tissue was removed from its receptacle and transferred to sterile culture plates where the tissue was divided into smaller 2-3 gramme parts. All the methods were carried out in the "cleanroom" of the Cell Production Unit by specialist personnel and fulfilling all the requirements for using the cells as therapy in humans.

In order to mechanically disaggregate the tissue, the fragments of thymic tissue were introduced in specific and disposable containers containing blades for disaggregating the tissue (gentleMACS™ C tubes, Miltenyi Biotic Ref. 130-096-334) and that also contained GMP TexMACS™ culture medium and 5% of antibiotic. The thymic tissue was disaggregated using the gentleMACS™ Octo Dissociator (Miltenyi Biotec). Upon completing the disaggregation, the tube was centrifuged, the supernatant was discarded and the cell precipitate containing the thymocytes was resuspended in 50 ml of Tex MACS medium containing 5% of antibiotic and was filtered using filters with a pore diameter of 40 μm to remove aggregates and tissue remnants. A quality and viability control was performed on the thymocyte suspension obtained. If viability is greater than 80% and there are no signs of contamination, the thyTreg cells are purified. Otherwise, the sample would be discarded.

An innovative element of the developed protocol is that it does not involve enzyme digestion nor is it any type of reagent, animal serum or method not compatible with the subsequent use of the cells as therapy in humans used.

1.3. Purification of the thyTreg Cells

The Treg cells were purified in cleanroom environments using a processing apparatus and a magnetic cell separator (MACS), approved by the corresponding legislation for use in cell therapy in humans. In this case, it was decided to use the CliniMACs® plus instrument (Miltenyi Biotec), for which purpose a closed circuit (CliniMACs® tubing set, Miltenyi Biotec) and CliniMACs® CD25 reagent (Miltenyi Biotec) were used. All the thymocytes isolated in the previous step were processed and introduced in the MACS system to purify the Tregs following the manufacturer's instructions. Once the cells were purified, a quality control was performed using flow cytometry to verify the viability, number and purity of the thyTreg cells. If viability is of at least 80% and purity of CD25+ cells is of at least 70% the purified cells are activated and cultured. Otherwise, the sample would be discarded.

1.4. Cultivation and Activation of the thyTreg Cells

The purified CD25+ cells were distributed in large cultivation receptacles (flasks) containing TexMACS™ medium and 5% of antibiotic, 600 U/ml of GMP interleukin 2 (IL-2) and a colloidal polymer nanomatrix (T Cell TransAct™ human, Miltenyi Biotec, Cat. No. 130-111-160) that makes it possible to contain and activate the thyTreg cells. The doses of T Cell TransAct™ human used were optimised in the present invention and ranged between 1:10 and 1:100.

Figure 1:
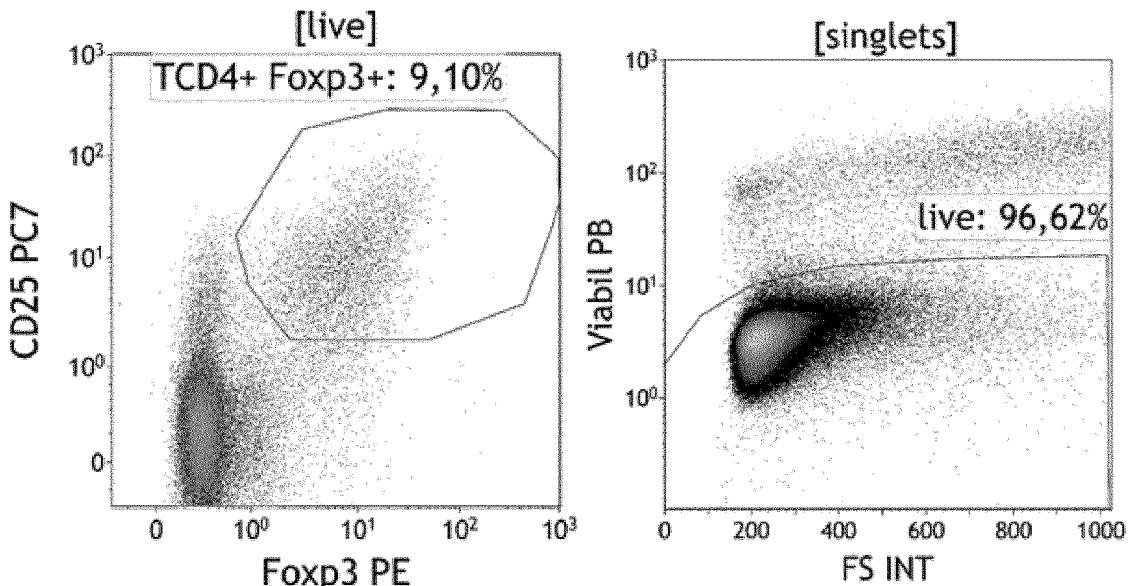
FIG. 1. Shows the results of purifying and enriching the thymus-derived thyTreg cells. The thymic tissue was taken from 5-month-old children. It shows the frequency of Treg cells in the total thymocytes prior to the purification protocol (A), and the viability (B) and purity (C) of CD25+Foxp3+ Treg cells in the final product obtained with the method of the invention.
Figure 1:
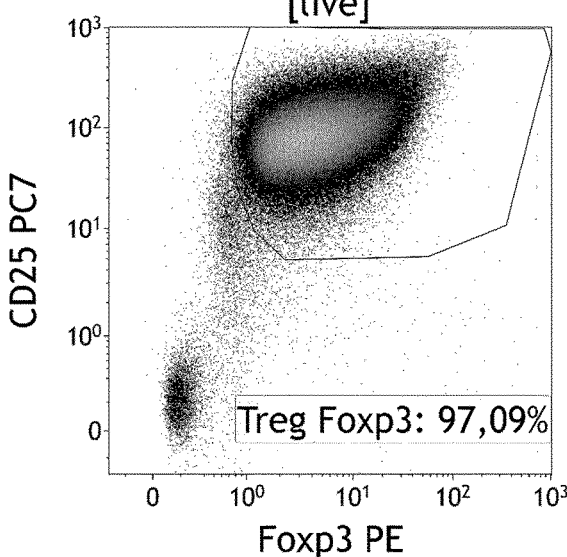

After three days of cultivation, the nanomatrix was removed by means of centrifugation and the thyTreg cells were kept under cultivation for another four days, regularly renewing the culture medium with antibiotic and IL-2. The results show that the proportion of CD25+Foxp3+ Treg cells in the total thymocytes after disaggregating the tissue was 9,10% in this example (FIG. 1A) and, after applying the protocol of the invention, a final product was obtained with a cell viability of 96% (FIG. 1B), and a thyTreg purity of CD25+Foxp3+ cells of more than 95% (FIG. 1C) (FIG. 1). Frequency of CD25+Foxp3+ cells was determined by flow cytometry (Gallios, Beckman coulter). We permeabilised cell membranes for intracellular staining of Foxp3 using the Anti-Human Foxp3 Kit (eBioscience). Then, we stained the cells with CD25 (Beckton Dickinson) and Foxp3 (eBiosciences) antibodies coupled with fluorochromes. Viability was calculated including a fixable viability dye in the staining procedure. In this example, processing a whole thymus of 26.17 gr. we produced a final product containing $13.7 \times 10^9$ (>13 billions) of thyTreg with the purity and viability mentioned above.

Practically all the protocols that exist in literature or which are used for the cultivation/expression of cells supplement the culture medium with bovine serums incompatible with the therapeutic use of the cells in humans. It is also common to use reagents such as particles coated with anti-CD3 and anti-CD28 (i.e., Dynabeads™) in the cultivation of Tregs to activate the cells, or rapamycin to increase the Treg purity of the product. The use of these reagents hinders the therapeutic use of the cells obtained or requires additional methods to fully remove the aforementioned particles before transferring the cells to the patient. On the contrary, the protocol herein described does not use any type of serum, drugs or reagents that make it incompatible with the therapeutic use of the cells in humans. Both the culture medium and the IL-2 are GMP and are allowed in the production of cells for clinical therapeutic use. Additionally, through this protocol, the colloidal polymer nanomatrix used in this example in thyTreg cells for the activation thereof is completely removed through simple centrifugation and, therefore, does not affect the quality and the yield of the cells and allows the subsequent use thereof in cell therapy.

1.5. Obtaining the Final thyTreg Product

After the seven days of cultivation have elapsed, the relevant quality, sterility and safety controls were performed (presence of microplasmas and genetic stability) with a successful outcome, thereby confirming that the product obtained fulfils all the requirements for the therapeutic use thereof in humans. Next, the necessary dose of thyTreg cells for cell therapy in the patient was dosed, taking into account the weight of the individual and the dose of the number of cells per kg determined in each case. The rest of the cells were cryopreserved to perform repeat doses in the future in the patient or for use in other patients or diseases.

Indicatively, the protocol of the invention enabled to obtain more than 13 billion thyTregs with a purity of more than 95%, a viability of more than 90% and a very high suppressive capacity. Such a number of cells would make it possible to prepare more than 1,000 doses of cell therapy for a patient less than 1 year old and hundreds of doses if used in older children or in adults. These yields in obtaining thyTreg cells are unheard of. To date, the protocols for purifying Tregs from peripheral blood obtain yields of less than 20 million cells, thereby requiring massive expansion protocols that require the use of different reagents and that significantly reduce the quality of the cells. The purities obtained with other protocols are clearly inferior, since there are activated cells in peripheral blood that can be retained as contaminants of the Tregs in the purification process. Additionally, the more differentiated or activated state of the cells present in peripheral blood makes the Treg cells obtained have lower survival and less suppressive capacity than those obtained by means of this thymus-based protocol of the invention, which significantly compromises their therapeutic usefulness.

Example 2. Analysis of the Suppressive Capacity of thyTreg Cells Obtained with the Protocol Described in Example 1

Figure 2:
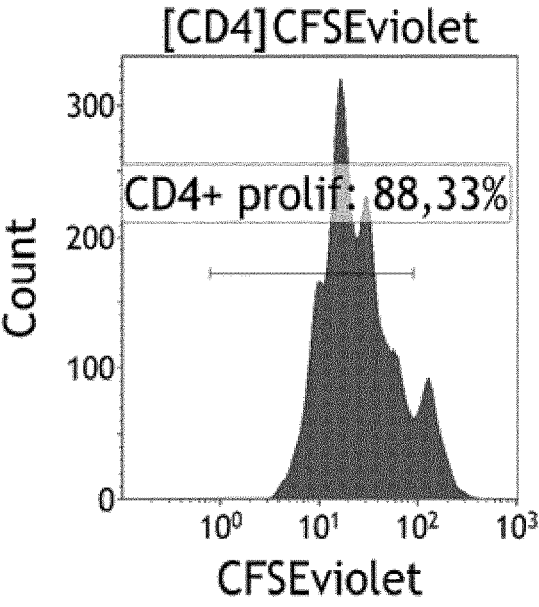
FIG. 2. Shows the suppressive capacity of the thymus-derived thyTreg cells. PBMC cells were dyed with CFSE, activated and co-cultivated alone or with thymus-derived thyTregs. Proliferation of responder T cells is measured as the reduction in the fluorescence intensity of CFSE staining. Activated TCD4+ and TCD8+ alone, proliferate in more than 87% after three days under cultivation. The presence of thyTregs decrease in more than 75% the proliferation of both activated CD4+ and CD8+ T cells.
Figure 2:
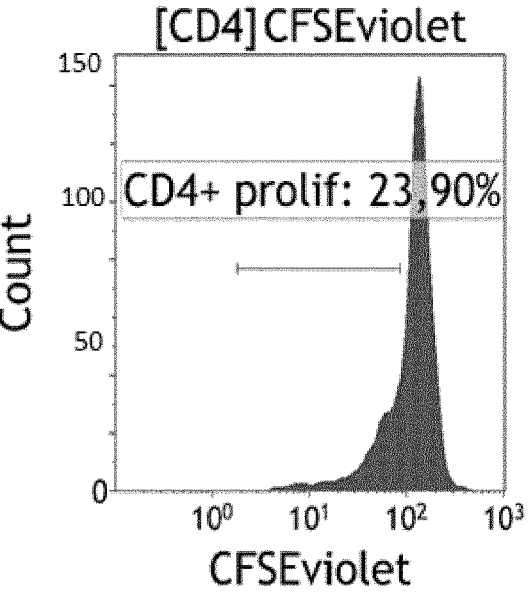
Figure 2:
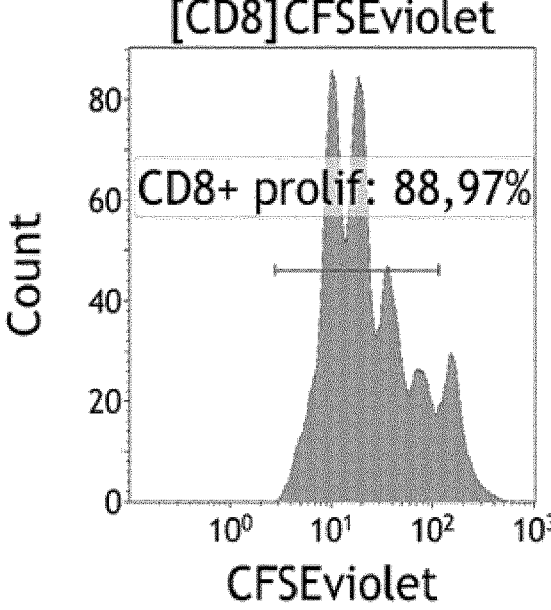
Figure 2:
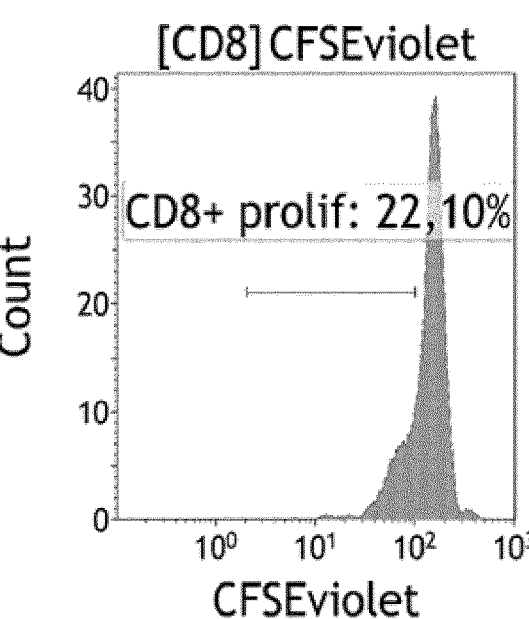

The suppressive capacity of the thyTreg cells produced in the previous example was analysed by measuring the capacity thereof to inhibit in vitro the cell proliferation of TCD4 and TCD8 lymphocytes, which are the primary mediators in cellular rejection to grafts and also autoimmune diseases. For such purpose, thyTreg cells were co-cultivated with allogeneic peripheral blood mononuclear cells (PBMC) dyed with CFSE (CellTrace™ CFSE proliferation kit, Invitrogen) in the ratio thyTreg:PBMC 1:2. The PBMCs were previously activated with PMA and Ionomycin (Sigma) in order to trigger the proliferation of T CD4+ and T CD8+ lymphocytes, comparing the proliferation of these cells with cultures in which the thyTregs were not included. Proliferation of responder T cells was measured by flow cytometry as the reduction in the fluorescence intensity of CFSE staining. CD3, CD4 and CD8 labeled antibodies (Beckman coulter) against the specific surface markers were used to distinguish between CD4+ and CD8+ T cells. The results confirmed that the presence of thyTregs decreases the proliferation of activated TCD4 and TCD8 cells by more than 70% (FIG. 2).

Figure 3:
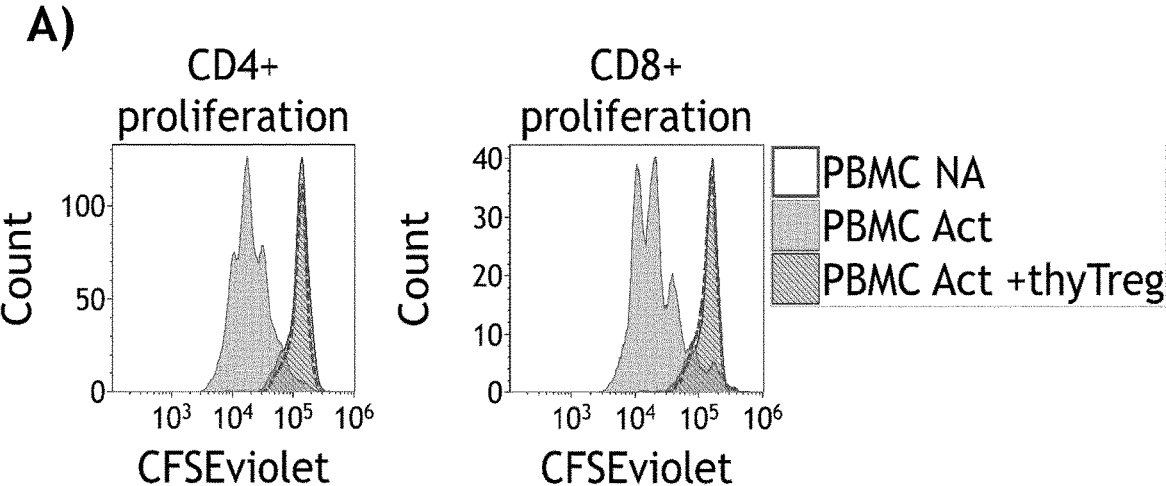
FIG. 3. Shows the efficacy of thyTreg suppressing the proliferation of allogenic CD4+ and CD8+ T cells. Non-activated (NA) T cells do not proliferate after 3 days culture (white); More than 80% of activated CD4+ and CD8+ T cells proliferate, observing several cycles of division (peaks) (grey area); however, the presence of thyTreg prevents the proliferation of these allogenic T cells in more than 80% (striped area) (A); The produced thyTreg population shows suppressive capacity against allogenic CD8+ and CD4+ T cells at various Treg-to-responder cell ratios (B).
Figure 3:
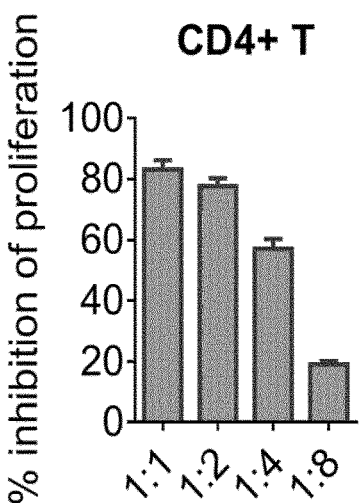
Figure 3:
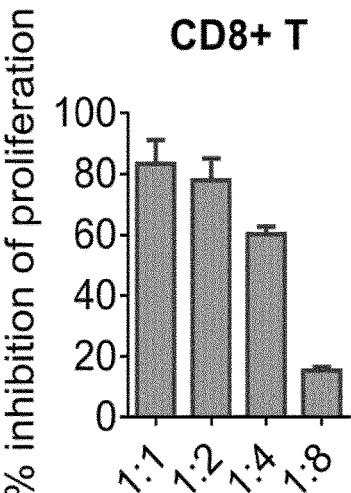

The efficacy of the obtained thyTreg population in suppressing the proliferation of allogenic CD4+ and CD8+ T cells was further investigated using distinct thyTreg:responder-cell ratios. Thy Tregs showed a very high suppressive capacity, inhibiting the proliferation of allogenic effector CD4+ and CD8+ T cells in more than 80% at a thyTreg:responder-cell ratio of 1:1 (FIG. 3A, 3B). This data further showed that a reduction of the proportion of thyTreg in the co-culture resulted in the inhibition of proliferation being also reduced, confirming that the suppression of proliferation is a specific effect of the thyTreg (FIG. 3B).

Figure 4:
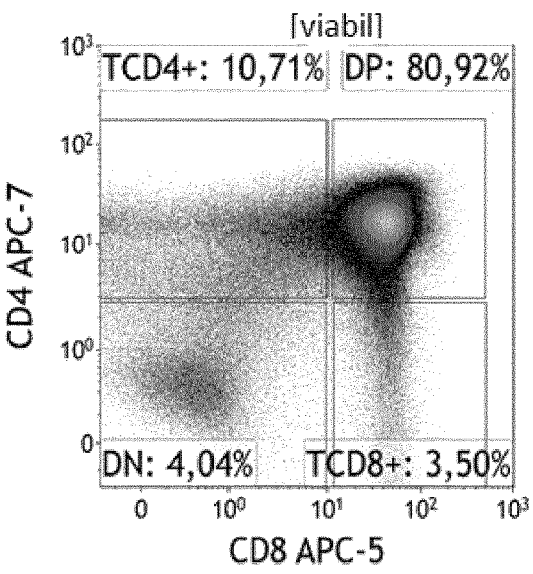
FIG. 4. Phenotype of total thymocytes obtained of thymic tissue (A); Purity in CD25+Foxp3+ cells in the final product of thyTreg (B); Distribution of thyTreg cells regarding CD4 and CD8 expression in the final product of thyTreg (C).
Figure 4:
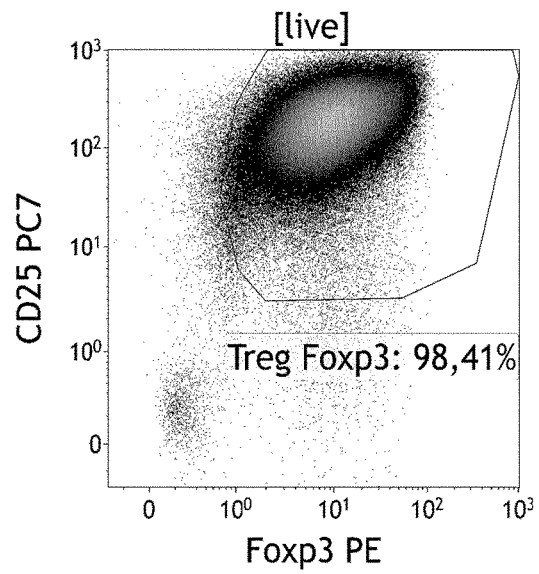
Figure 4:
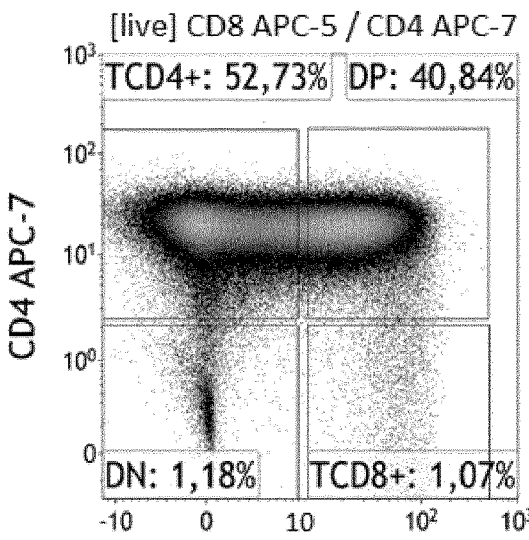

Example 3. Not Depleting the CD8+ Positive Cell Population Provides a Higher Yield of Treg Cells The vast majority (80%) of the total thymocytes that are isolated from the thymus are double positive (CD4+CD8+) cells (FIG. 4A). The inventors have unexpectedly shown that a very high proportion of Treg cells are inside this DP fraction. Indeed, it has been shown by the inventors that around 41% of the thyTreg cells population obtained as final product when following the protocol described in Example 1 (at day 7 of culture) are DP cells (FIG. 4B, 4C). Thus, a previous depletion of the CD8+ cells as described by Dijke I. E., et al., 2016 or MacDonald et al. 2017, where a CD4+CD8-CD25+ was selected prior to Treg cells stimulation and expansion, will eliminate completely the DP fraction, and consequently the Foxp3+DP population will not be present in the final product, the recovery of CD25+ Foxp3+ cells decreasing dramatically. Moreover, without willing to be bound by theory, due to its less-differentiated phenotype, the Treg cells comprised in DP fraction likely have a higher survival, plasticity and stability of their suppressive capacity.

Figure 5:
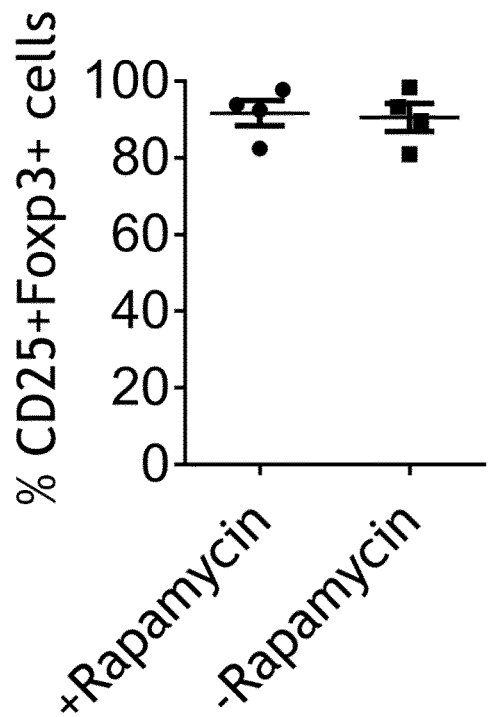
FIG. 5. Differences in purity of CD25+Foxp3+ cells (A) and in the fold expansion (B) between the same protocol employing rapamycin (+rapamycin) or without rapamamycin (−Rapamycin).
Figure 5:
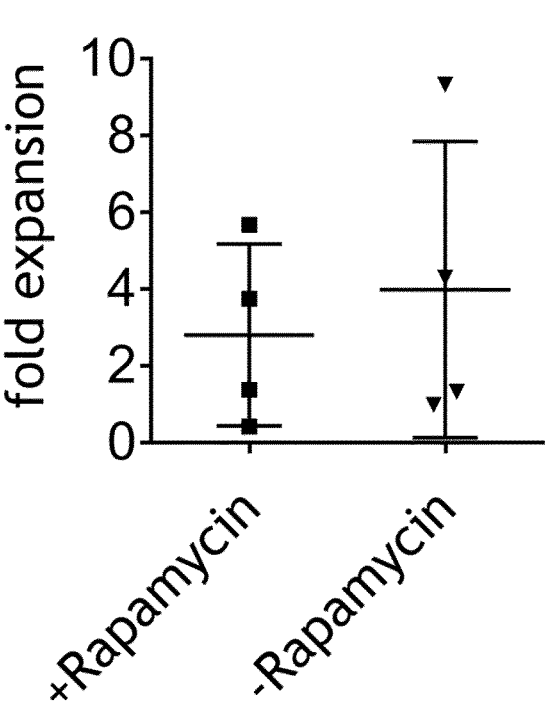

Example 4. The Employment of Rapamycin is not Required to Obtain a Highly Pure thyTreg Product Rapamycin is an immunosuppressant that inhibits the activation of T cells and is routinely used in Treg cell cultures. In the presence of high doses of IL-2 in vitro, rapamycin induces the proliferation of Treg and impairs the proliferation of effector T cells. We compared the presence and absence of 100 ng/ml of rapamycin in our cultures obtaining similar results regarding CD25+Foxp3+ purity (FIG. 5A). Interestingly, Treg proliferation after 7 days of culture was slightly higher in the absence of rapamycin (FIG. 5B). Avoiding the employment of rapamycin in the method to produce thyTreg is likely going to facilitate obtaining authorization of the governmental drug agencies to use these cells as a therapy in humans. Thus, avoiding the use of rapamycin entails a further advantage in our procedure.

Example 5. Comparison of the Colloidal Nanomatrix (T Cell TransAct™) with CD3/CD28 Beads for thyTreg Stimulation "Dynabeads CD3/CD28 CTS™" from Invitrogen is employed in most of the protocols to cultivate or expand Treg cells. It comprises magnetic beads conjugated to agonistic monoclonal antibodies against human CD3 and CD28. These beads need to be removed after Treg activation and before administration of cells to the patient, employing a magnetic sorting that entails a significant loss (>25%) of cells after Dynabeads CD3/CD28 CTS™ are removed through the magnetic column.

The protocol described in Example 1 replaces the employment of Dynabeads CD3/CD28 CTS™ by MACS GMP T Cell TransAct™ (Miltenyi Biotec) which consists in a colloidal polymeric nanomatrix which activates T cells. The inventors have been pioneers in employing this product for the activation of Treg cells.

The advantage of using the nanomatrix for activation purposes is that it could be easily removed by a simple centrifugation and replacement of medium, without a significant loss of cells.

The inventors compared how the two activators affect the purity, the expression of functionality markers and the expansion of the Treg cells after culture. As showed, CD25+ Foxp3+ purity is slightly higher when using T Cell TransAct™ (89%) rather than Dynabeads CD3/CD28 CTS™ (82%) (FIG. 6A, 6B). Whereas the activation marker HLA-DR as well as the fold expansion (number of CD25+Foxp3+ cells before and after activation and expansion) seem to be comparable, the markers associated with Treg function (such as CTLA-4 and CD39) showed higher expression when using T Cell TransAct™ in comparison with Dynabeads CD3/CD28 CTS™ (FIG. 6C, 6D).

Example 6. Treg Cells Produced with the Protocol of the Invention have an Stable Foxp3 Expression and Maintains the IL-10 Production Capacity Numerous studies have shown that Treg cells obtained from peripheral blood can loss their Foxp3 expression and suppressive phenotype in the presence of pro-inflammatory cytokines, and even Treg can switch their phenotype in these conditions adquiring a phenotype of Th1, Th17 or Th2 cytokine secreting cell. Therefore, a potential limitation to Treg-based therapy is instability and plasticity of therapeutic Tregs, especially under inflammatory conditions. We analysed the stability of Foxp3 expression and the capacity to produce IL-10 of the thyTreg obtained in the final product in the presence of an inflammatory environment. For that, we cultured thyTreg in the presence of IL-1β, IL-6, TNFα. The results, indicate that Foxp3 expression (FIG. 8A) and capacity to produce IL-10 (FIG. 8B) was comparable between standard culture conditions and in the presence of an inflammatory environment.

Example 7. Treg Cells Produced with the Protocol of the Invention Express Low Levels of Immunogenic Markers It has further been determined by the inventors that the Treg cell or cell population of the invention would be suitable for its use in the treatment of autoimmune diseases, GVHD and other immune disorders in patients different to the subject from which the cells were obtained (allogenic use). In order to be suitable for use as allogeneic cell therapy, the Treg cells must have a low immunogenicity to avoid being recognized and destroyed by the immune system of the recipient. Moreover, allogenic Treg must have the capacity to suppress immune cells from the recipient to exert their suppressive function (as shown in Example 2).

Figure 7:
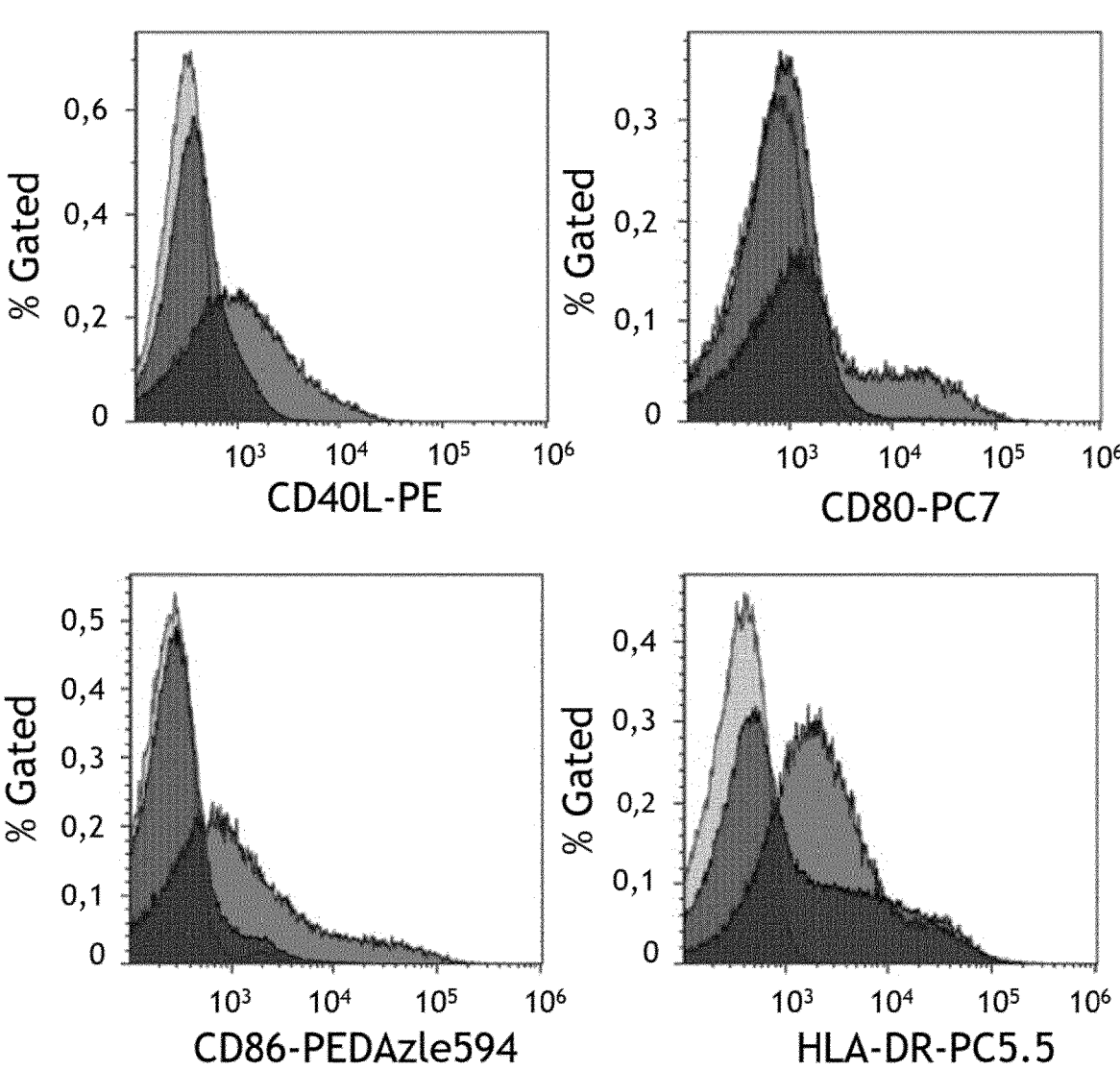
FIG. 7. ThyTreg produced with our protocol (dark grey) have a lower expression of immunogenic markers than conventional CD4+ T cells obtained from adult peripheral blood (grey). Isotypic control is represented as a light grey area.

Generally, cells that express MHC molecules (HLA-DR) can stimulate and be recognized by T cells if they possess appropriate co-stimulatory molecules (CD40, CD40L, CD80, CD86 . . . ). The inventors determined by flow cytometry the expression of CD40L, CD80, CD86 and HLA-DR (Beckman coulter) in ThyTreg cells obtained in Example 1 and in conventional CD4+ cells obtained from adult peripheral blood. They demonstrated that thyTregs produced with by the protocol of the invention express lower levels of these immunogenic markers compared to conventional CD4+ T cells from peripheral blood (FIG. 7). Since the obtained ThyTreg cell population has lower levels of co-stimulatory molecules, these are likely to be incapable of inducing a robust immune response in an allogenic recipient by direct antigen presentation, or at least immune activation will occur to a lesser extent than with conventional CD4+ T cells.

CLAUSES

1. An in vitro method for obtaining regulatory T cells from isolated thymic tissue comprising the following stages:
   a. mechanically disaggregating the thymic tissue using a tissue dissociator in the presence of a GMP culture medium,
   b. filtering the product obtained after stage (a), and resuspending the precipitate comprising thymocytes in the GMP culture medium, c. purifying the regulatory T cells from the product obtained after stage (b),
   d. cultivating, for at least three days, the regulatory Tcells obtained after stage (c) in the presence of a T cell activator, of GMP culture medium and IL-2,
   e. removing the T cell activator from the culture medium of stage (d), and
   f. optionally, keeping the regulatory T cells in culture medium for at least another four days.

2. The method, according to clause 1, wherein the purification of stage (c) is carried out using the CliniMACs® plus instrument in the presence of a specific murine IgG1 isotype anti-human CD25 monoclonal antibody conjugated with superparamagnetic particles.

3. The method, according to anyone of clauses 1 or 2, wherein the T cell activator of stage (d) is a colloidal polymer nanomatrix conjugated with humanised CD3 and CD28 agonists.

4. The method, according to anyone of clauses 1 to 3, wherein the removal of stage (e) is carried out by means of centrifugation.

5. The method, according to anyone of clauses 1 to 4, wherein the thymic tissue comes from a human.

6. The method, according to anyone of clauses 1 to 5, wherein the thymic tissue comes from a human between 0 and 16 years old.

7. The method, according to clause 6, wherein the thymic tissue comes from a human between 0 and 24 months old.

8. The method, according to anyone of clauses 1 to 7, which further comprises an additional step (g) comprising the cryopreservation of the regulatory T cells obtained.

9. A regulatory T cell or population of regulatory T cells obtained with the method, according to anyone of clauses 1 to 8, wherein said regulatory T cell expresses at least the CD3, CD25 and Foxp3 markers.

10. The regulatory T cell or population of regulatory T cells, according to clause 9, wherein said cell comprises a nucleic acid sequence encoding a chimeric antigen receptor.

11. The regulatory T cell or population of regulatory T cells, according to clause 10, wherein the antigen is an antigen present in an effector cell of the immune system.

12. A pharmaceutical composition comprising the regulatory T cell or the population of regulatory T cells, according to anyone of clauses 9 to 11.

13. The pharmaceutical composition, according to clause 12, further comprising an excipient and/or pharmaceutically acceptable carrier.

14. A kit for carrying out the method, according to anyone of clauses 1 to 8, comprising a GMP culture medium, anti-CD25 antibodies, a T cell activator and IL-2.

15. The kit comprising the regulatory T cell or population of regulatory T cells, according to anyone of clauses 9 to 11, or the pharmaceutical composition, according to anyone of clauses 12 or 13, and an appropriate medical device for injecting cells into a subject.

16. Use of the regulatory T cell or population of regulatory T cells, according to anyone of clauses 9 to 11, or of the pharmaceutical composition, according to anyone of clauses 12 or 13, to manufacture a medicament.

17. The use, according to clause 16, wherein the medicament is a cell therapy medicament.

18. The use, according to anyone of clauses 16 or 17, wherein the medicament is for treating and/or preventing a pathological condition selected from the list consisting of: autoimmune disease, inflammatory processes, allergy, graft-versus-host disease and/or immune rejection in transplanted individuals.

19. The use, according to clause 18, wherein the individual with the pathological condition is human.

20. The use, according to anyone of clauses 18 or 19, wherein the medicament is used in the treatment and/or prevention of immune rejection in transplanted subjects.

21. The use, according to clause 20, wherein the transplant is a solid organ transplant.

22. The use, according to clause 21, wherein the solid organ is the heart.

23. The use, according to anyone of clauses 16 to 22, wherein the medicament is administered in combination with at least one immunosuppressive drug.

24. The use, according to anyone of clauses 16 to 23, wherein the medicament is administered upon completing a previous therapy using immunosuppressive drugs.

The invention claimed is:

1. A cell population comprising regulatory T (Treg) cells obtained from isolated thymic tissue (a thyTreg cell population), wherein said thyTreg cell population comprises CD4$^+$ CD8 Foxp3$^+$ cells;

wherein said thyTreg cell population comprises at least 90% of CD4$^+$CD25$^+$Foxp3$^+$ cells;

wherein said thyTreg cell population does not comprise effector T cells; and wherein said thyTreg cell population is obtainable by a method comprising the following steps:

(a) disaggregating the thymic tissue;

(b) filtering a product obtained after stage (a), and resuspending a precipitate comprising thymocytes in a culture medium;

(c) isolating CD25$^+$ cells from the product obtained after stage (b);

(d) culturing a cell population obtained after stage (c) in a culture medium in the presence of a T cell activator and IL-2, wherein said T cell activator comprises at least CD3 and CD28 agonists; and (e) removing the T cell activator from the culture medium of stage (d);

wherein prior to step (d), the cell population has not been depleted of CD8$^+$ cells.

2. The thyTreg cell population according to claim 1, wherein said thyTreg cell population comprises at least 95% of CD4$^+$CD25$^+$Foxp3$^+$ cells.

3. The thyTreg cell population according to claim 1, wherein the cells from said thyTreg cell population have been genetically modified.

4. The thyTreg cell population according to claim 3, wherein the cells from said thyTreg cell population comprise a nucleic acid sequence encoding a chimeric antigen receptor.

5. A pharmaceutical composition comprising the thyTreg cell population according to claim 1, wherein said pharmaceutical composition further comprises an excipient or pharmaceutically acceptable carrier, or both.

6. A method for treating, preventing, or both, a pathological condition selected from the group consisting of: graft-versus-host disease and immune rejection in a transplanted or grafted individual, wherein said method comprises autologous or allogeneic administration of a therapeutically effective amount of the thyTreg cell population according to claim 1 to the individual.

7. The method according to claim 6, wherein the individual is a human.

8. The method according to claim 6, wherein said method is for treatment, prevention, or both, of immune rejection in transplanted individuals.

9. The method according to claim 6, wherein the thyTreg cell population is administered in combination with at least one immunosuppressive drug, or wherein the thyTreg cell population is administered upon completing a previous therapy using immunosuppressive drugs.

10. The method according to claim 6, wherein said method comprises the allogeneic administration of the thyTreg cell population.

11. A kit comprising the thyTreg cell population according to claim 1, and an adequate medical device for its administration to an individual.

12. A method for obtaining a thyTreg cell population as defined in claim 1 from isolated thymic tissue, wherein said method comprises the following steps:

(a) disaggregating the thymic tissue;

(b) filtering a product obtained after stage (a), and resuspending a precipitate comprising thymocytes in a culture medium;

(c) isolating CD25$^+$ cells from the product obtained after stage (b);

(d) culturing the cell population obtained after stage (c) in a culture medium in the presence of a T cell activator and IL-2, wherein said T cell activator comprises at least CD3 and CD28 agonists; and (e) 9 removing the T cell activator from the culture medium of stage (d);

wherein prior to step (d), the cell population has not been depleted of CD8$^+$ cells.

13. The method according to claim 12, wherein step (a) comprises mechanically disaggregating the thymic tissue in the presence of a culture medium and without using enzymes.

14. The method according to claim 12, wherein isolation of CD25$^+$ cells in step (c) comprises the use of magnetic beads conjugated to antibodies against CD25.

15. The method according to claim 12, wherein the T cell activator of stage (d) is a colloidal polymer nanomatrix conjugated with humanised CD3 and CD28 agonists.

16. The method according to claim 12, wherein the T cell activator of stage (d) is used in a T cell activator:cell ratio range between 1:10 and 1:100.

17. The method according to claim 12, wherein the cells are cultured in step (d) for at least 2 or 3 days.

18. The method according to claim 12, wherein the cells are cultured in step (d) in the absence of rapamycin.

19. The method according to claim 12, wherein the removal of stage (e) is carried out by means of centrifugation.

20. The method according to claim 12, wherein said culture medium is a GMP culture medium.

21. The method according to claim 12, wherein said culture medium further comprises an antibiotic.

22. The method, according to claim 12, wherein the thymic tissue comes from a human.

23. The method according to claim 12, wherein the thymic tissue comes from a human between 0 and 16 years old.

24. The method, according to claim 12, which further comprises an additional step (g) comprising cryopreservation of the regulatory T cells obtained.

25. A method for inducing or restoring immune tolerance in an individual, wherein said method comprises administration of the thyTreg cell population of claim 1 to said individual in a therapeutically effective amount; and wherein said individual is a transplanted or grafted individual, or an individual who has graft-versus-host disease.

26. The thyTreg cell population according to claim 1, wherein step (a) comprises mechanically disaggregating the thymic tissue.

27. The method according to claim 12, wherein step (a) comprises mechanically disaggregating the thymic tissue.

28. The thyTreg cell population according to claim 1, wherein the method to obtain said thyTreg cell population further comprises the following step:

(f) further culturing the regulatory T cells in a culture medium in the presence of IL-2.

29. The method according to claim 12, wherein said method further comprises the following step:

(f) further culturing the regulatory T cells in a culture medium in the presence of IL-2.

30. The method according to claim 29, wherein in step (f) the regulatory T cells are cultured for another one to seven days in the presence of IL-2.

31. The method according to claim 29, wherein the cells are cultured in step (f) in the absence of rapamycin.

\* \* \* \* \*